US012568961B2

(12) United States Patent
Hill

(10) Patent No.: US 12,568,961 B2
(45) Date of Patent: Mar. 10, 2026

(54) MULTI-LAYER TRUE SPHERICAL CHITOSAN ENCAPSULATION OF ABSOLUTE (ESSENTIAL) OILS FOR USE IN PESTICIDAL ACTIVITY

(71) Applicant: GroPro Corporation, Burnsville, MN (US)

(72) Inventor: Jeff Hill, Burnsville, MN (US)

(73) Assignee: GroPro Corporation, Burnsville, MN (US)

( * ) Notice: Subject to any disclaimer, the term of this patent is extended or adjusted under 35 U.S.C. 154(b) by 341 days.

(21) Appl. No.: 18/476,743

(22) Filed: Sep. 28, 2023

(65) Prior Publication Data

US 2025/0098666 A1     Mar. 27, 2025

Related U.S. Application Data

(60) Provisional application No. 63/585,574, filed on Sep. 26, 2023.

(51) Int. Cl.

| | |
|---|---|
| *A01N 25/28* | (2006.01) |
| *A01N 25/00* | (2006.01) |
| *A01N 25/10* | (2006.01) |
| *A01N 25/14* | (2006.01) |
| *A01N 25/30* | (2006.01) |
| *A01N 27/00* | (2006.01) |
| *A01N 31/02* | (2006.01) |
| *A01N 43/40* | (2006.01) |
| *A01N 43/90* | (2006.01) |
| *A01N 61/02* | (2006.01) |
| *A01N 65/06* | (2009.01) |
| *A01N 65/08* | (2009.01) |
| *A01N 65/18* | (2009.01) |
| *A01N 65/20* | (2009.01) |
| *A01N 65/22* | (2009.01) |
| *A01N 65/26* | (2009.01) |
| *A01N 65/28* | (2009.01) |
| *A01N 65/36* | (2009.01) |
| *A01N 65/40* | (2009.01) |
| *A01N 65/42* | (2009.01) |
| *A01N 65/44* | (2009.01) |
| *A01P 3/00* | (2006.01) |
| *A01P 5/00* | (2006.01) |
| *A01P 7/04* | (2006.01) |
| *A01P 17/00* | (2006.01) |
| *B82Y 5/00* | (2011.01) |
| *B82Y 40/00* | (2011.01) |

(52) U.S. Cl.
CPC .......... *A01N 25/28* (2013.01); *A01N 25/006* (2013.01); *A01N 25/10* (2013.01); *A01N 25/14* (2013.01); *A01N 25/30* (2013.01); *A01N 27/00* (2013.01); *A01N 31/02* (2013.01); *A01N 43/40* (2013.01); *A01N 43/90* (2013.01); *A01N 61/02* (2013.01); *A01N 65/06* (2013.01); *A01N 65/08* (2013.01); *A01N 65/18* (2013.01); *A01N 65/20* (2013.01); *A01N 65/22* (2013.01); *A01N 65/26* (2013.01); *A01N 65/28* (2013.01); *A01N 65/36* (2013.01); *A01N 65/40* (2013.01); *A01N 65/42* (2013.01); *A01N 65/44* (2013.01); *A01P 3/00* (2021.08); *A01P 5/00* (2021.08); *A01P 7/04* (2021.08); *A01P 17/00* (2021.08); *B82Y 5/00* (2013.01); *B82Y 40/00* (2013.01)

(58) Field of Classification Search
None
See application file for complete search history.

(56) References Cited

FOREIGN PATENT DOCUMENTS

CN            114588128 A  *  6/2022   ............. A61K 9/501

* cited by examiner

*Primary Examiner* — Alton N Pryor
(74) *Attorney, Agent, or Firm* — LSIP Law LLC

(57)            ABSTRACT

Some embodiments include a method of chitosan encapsulation of pesticidal active ingredients. The method includes adding a first active ingredient to a centrifuge, adding a solution containing chitosan into the centrifuge, centrifuging the chitosan-active ingredient mixture to create nanoparticle spheres of a first diameter, collecting the nanoparticle spheres of a first diameter, adding the nanoparticle spheres, a second active ingredient, and a chitosan solution into a centrifuge, and centrifuging to create nanoparticle spheres of a second diameter larger than the first diameter, and collecting the nanoparticle spheres of a second diameter.

16 Claims, 9 Drawing Sheets

MULTI-LAYER TRUE SPHERICAL CHITOSAN ENCAPSULATION OF ABSOLUTE (ESSENTIAL) OILS FOR USE IN PESTICIDAL ACTIVITY

BACKGROUND

The present disclosure relates to systems and methods involving chitosan encapsulation of pesticidal active ingredients. Chitosan encapsulation is a versatile technique that allows for the controlled release of substances encapsulated within chitosan particles or capsules. The chitosan polymer has several unique properties that make it an ideal material for encapsulation, including its biocompatibility, biodegradability, and ability to form stable complexes with a wide range of molecules.

Chitosan encapsulation has emerged as a promising technique for developing effective and environmentally friendly pesticides. Chitosan, derived from chitin found in crustacean shells, is a natural polymer with inherent properties such as biocompatibility, biodegradability, and low toxicity, which make it a highly attractive material for use in pesticide encapsulation.

Chitosan particles can be used to encapsulate pesticides, which can then be released in a controlled manner to their target organisms, reducing the negative impact on non-target organisms and the environment. This technology has been shown to improve the efficacy of pesticides, reduce the amount of pesticide needed, and prolong the duration of pesticide activity.

SUMMARY

The present disclosure relates to systems and methods for multi-layer encapsulation of active ingredients in organic polymers, with a focus on the use of chitosan as the main polymer. The method allows for the encapsulation of any liquid ingredient, regardless of its polarity or amphiphilicity, in chitosan. Preferred embodiments include the encapsulation of nanoparticles of active ingredients in true spheres of chitosan, achieved by spraying the active ingredients with chitosan and centrifuging at 4000-8000 rps in a centrifugal apparatus. The encapsulation process can be repeated with multiple layers of active ingredients and chitosan, with the layers alternating between the two. The method of producing the second layer involves drying the original true spherical nanoparticles. In some embodiments, non-"true" spherical encapsulations can be produced by slightly altering the rps of the centrifuge, allowing for multiple layers of chitosan and active ingredients, but with less stability and slower release compared to true spheres. The disclosed method can be applied to various active ingredients, with preferred embodiments using active ingredients used in pesticidal formulations/compositions.

This method can encapsulate any liquid ingredient, regardless of its polarity, viscosity, or amphiphilic nature, in chitosan. The preferred embodiments include wrapping nanoparticles of active ingredients in true spheres of chitosan. These true spheres can be created by spraying the active ingredients with chitosan and centrifuging at a specific speed in a centrifugal apparatus. The rps used in the encapsulation method may change from 4000-8000 rps depending on the active ingredient used, its polarity, and its viscosity. The method also allows for the creation of multiple layers of active ingredients and chitosan by drying the original true spherical nanoparticles.

The active ingredients used in this invention can be any liquid substance but are preferably one of the active ingredients used in pesticidal formulations/compositions. The chitosan used in this invention can be any type of chitosan, but organically-derived chitosan is preferred when creating pesticides for organic agricultural use. The chitosan may also be coated with crosslinking agents, such as sodium triphosphate pentabasic (STP), to code it to decompose when specific triggers occur, such as pH, polarity, and time. This coding allows for the slow release of active ingredients in a controlled manner. Additionally, the invention includes chitosan wraps coded to degrade based on specific pH environments, which can be beneficial in targeting pests that thrive in certain pH environments.

Multi-layer chitosan encapsulation offers numerous advantages over single-layer encapsulation. The additional layers provide increased stability, allowing for slower and more controlled release of the active ingredients. This can result in improved efficacy, reduced toxicity to non-target organisms, and reduced environmental impact.

The disclosed method allows for the creation of true spherical nanoparticles of chitosan encapsulating the active ingredients, resulting in a highly stable and effective product. The method also enables the production of non-"true" spherical encapsulations, albeit with less stability and slower release, which may still be useful in certain applications.

The disclosed method has a wide range of potential applications, including in the development of more effective and environmentally friendly pesticides. The ability to encapsulate any liquid ingredient in chitosan makes this method highly versatile and suitable for use with a variety of active ingredients. Some embodiments may include multi-layer encapsulation of medicinal active ingredients used to target specific locations in the body, sanitizing active ingredients used in cleaning agents, aromatic active ingredients for perfumes, or other liquid ingredients that would benefit from a slow-release method of administration.

Additionally, the disclosed multi-layer chitosan encapsulation method allows for the alternating use of different active ingredients between layers. This means that each layer may contain a different active ingredient, providing a wide range of applications. For example, one layer may contain a fertilizer, the next layer may be a nematicide, and the following layer may be a fungicide. This alternating encapsulation technique can be used to create a single, multi-functional product that can provide multiple benefits in one application. This approach offers the potential for improved efficiency and reduced application costs, as well as reduced environmental impact by limiting the need for multiple separate applications.

Some embodiments include a system for a formulation of nanoparticles used for protecting plants from pests while promoting plant growth, the formulation including a solution comprising at least one of a filler, an extender, a wetting agent, a disintegrant, and a surfactant, nanoparticles with relatively spherical layers in the solution, the nanoparticles comprising, a relatively spherical liquid core layer comprising a pesticidal active ingredient, a relatively spherical first layer comprising chitosan, the relatively spherical first layer wrapping the relatively spherical liquid core layer and located directly on the relatively spherical liquid core layer, a relatively spherical second layer comprising a fertilizing active ingredient, the spherical second layer wrapping the first spherical layer, a relatively spherical final layer comprising chitosan, the relatively spherical final layer being the outermost relatively spherical layer of the nanoparticle, wherein the formulation is applied to an environment, and the pesticidal active ingredient and the fertilizing active ingredient are released into the environment.

In some embodiments, the nanoparticles are created using a centrifuge. In some embodiments, the relatively spherical liquid core layer, relatively spherical first layer, relatively spherical second layer, and relatively spherical final layer may be one of a "true" sphere or a non-"true" sphere. In some embodiments, the nanoparticles have a diameter of 20-200 nm. In some embodiments, the environment is one of a field, lawn, wooded area, forest, jungle, swamp, body of water, house, and office.

In some embodiments, the at least one of a filler, an extender, a wetting agent, a disintegrant, and a surfactant is one of water and alcohol. In some embodiments, the at least one of a filler, an extender, a wetting agent, a disintegrant, and a surfactant is one of, dextrin, calcium carbonate, lactose, propylene glycol, liquid paraffin, and saline. In some embodiments, wherein the one of plant essential oil and plant extract is oxymatrine, geraniol, castor oil, castor extract, linseed, cedar, cinnamon, mint, peppermint, citronella, clove, corn, rosemary, cottonseed, sesame, garlic, soybean, thyme, geranium, lemongrass, tea tree, white mineral oil, citrus, spearmint, and a mixture thereof.

Some embodiments include a specific mode of action used by the pesticidal active ingredient in the formulation, wherein the mode of action is one of membrane disruption, substrate deprivation, binding to cell wall complexes, enzyme inactivation, GABA inhibition, acetylcholine inhibition, paralysis, protein binding, inactivation of disulfide bridges, and interaction with eucaryotic DNA. In some embodiments, more than one mode of action is used.

Some embodiments include a relatively spherical third layer comprising one of the pesticidal active ingredient and the fertilizing active ingredient, the relatively spherical third layer being located somewhere between the relatively spherical core layer and the relatively spherical final layer. In some embodiments, there is a layer containing propolis. In some embodiments, the fertilizing active ingredient is one of propolis, cytokinin, gibberellins, auxins, abscisic acid, brassinosteroids, fucoxanthin, jasmonic acid, salicylic acid, humic acid, fulvic acid, and kelp extract. In some embodiments, the fertilizing active ingredient is one of bentonite and urea. In some embodiments, the fertilizing active ingredient has been chelated with one of EDTA, DTPA, EDDS, HEDTA, IDHA, and Fulvic acid.

4

Figure 9:
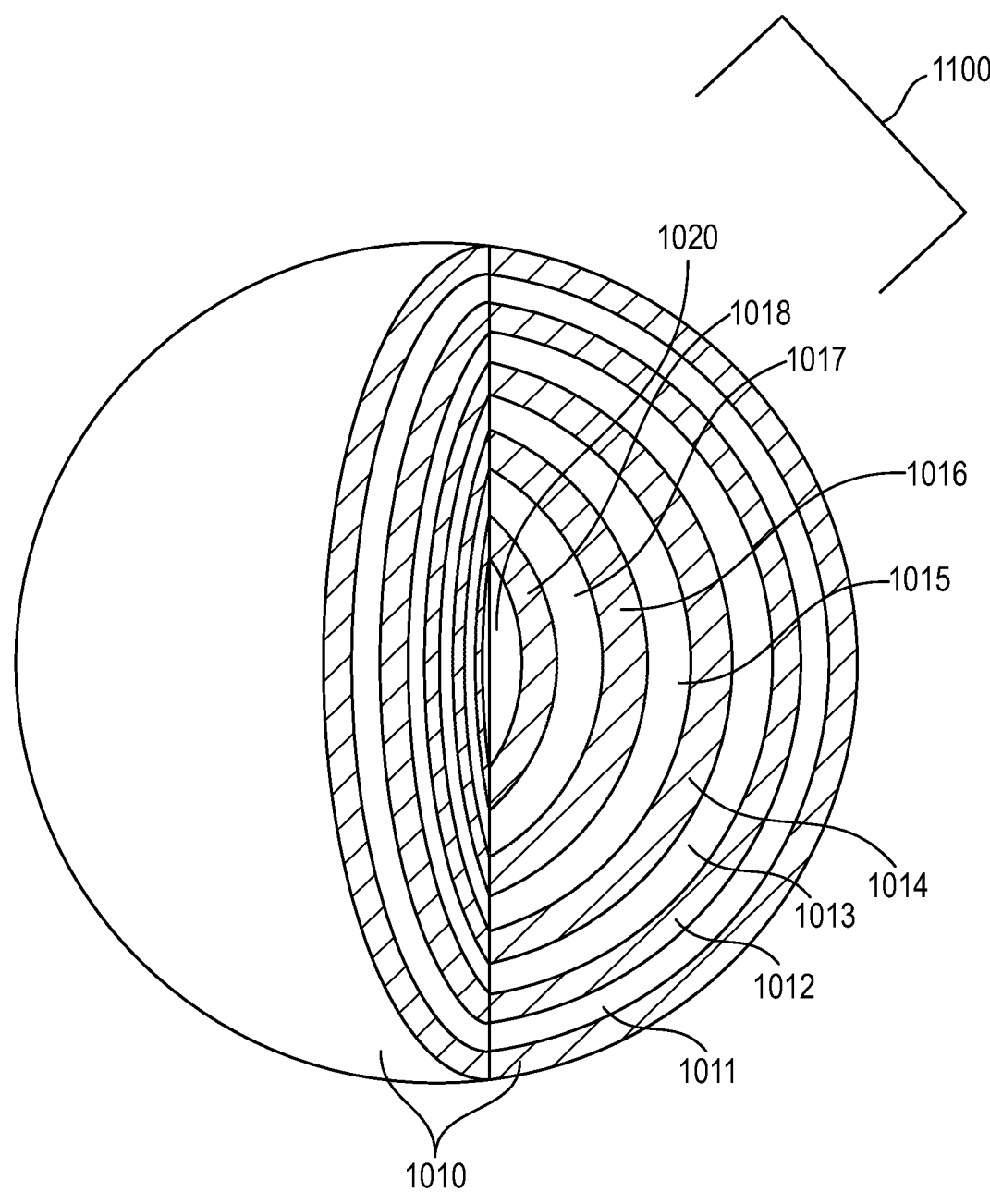

FIG. 9 is a sectional representative view of the cross-section of a 10-layer multi-layer chitosan encapsulated nanoparticle sphere.

DETAILED DESCRIPTION OF EXEMPLARY EMBODIMENTS

The figures are described below. Before the embodiments are to be explained in detail, it is to be understood that the presently disclosed subject matter is not limited in application or process to the details stated, as there are other embodiments and methods of carrying out and practicing the presently disclosed subject matter than those described. As such, the language used below is not limiting and states what may be used but may not necessarily be completely exhaustive.

Exemplary compositions, formulations and methods are disclosed below.

I. Overview
II. Encapsulation of Essential Oils
III. Production and Distillation of Essential Oils
IV. Controlling Nematodes
V. Controlling Mosquitos
VI Controlling Bacteria
VII. Controlling Insects
VIII. Controlling Fungus
IX. Controlling Nematodes and Fungus
X. Controlling Larvae and Insects with Oxymatrine
XI. Controlling Insects with Tea Saponin
XII. Controlling Various Insects with Geraniol
XIII. Controlling Black Sigatoka
XIV. Increasing Flower Hold and Bee Attraction
XV. Lotion for Repelling of Mosquitos
XVI. Neurotransmitter Inhibition
XVII. Hypersonic Distillation
XVIII. Multi-layer Chitosan Encapsulation

I. OVERVIEW

Insecticides have 5 major classification groups; (1) physical poisons, (2) protoplasmic poisons, (3) respiratory poisons, (4) nerve poisons, and (5) poisons of a more general nature.

The major groups of pests may include fungi, insects, nematodes, bacteria, snails, larvae, etc.

Many of the compositions contained in the present disclosure relate to increasing the yield of certain plant groups as well as protecting from pests using a single composition. Specific pests may be contained in the disclosure, but the formulations may kill more than the specified pests.

Certain ingredients may also be extracted from certain cultures of fungus or bacteria. Some formulations may use certain acids or bases active ingredients. Some formulations may include the conjugate acid or base of any active ingredient disclosed in the present disclosure.

As used herein, "essential oil" may be exchanged with "absolute oil" to provide stronger formulations without the use of certain alcohols in the final compositions.

II. ENCAPSULATION OF ESSENTIAL OILS

Some embodiments are related to a formulation for encapsulating pesticides, fungicides, insecticides, and pharmaceuticals derived from natural substances and found to be environmentally friendly. They, in turn, exhibit highly effective control mechanisms without causing plant or human phytotoxicity.

In the present invention, multiple types of crosslinker agents and raw materials were looked at to establish the highest-performing combination allowing for the highest encapsulation.

In some embodiments, the essential oils must be extracted from certain plants before they can be used in a pesticide formulation. The methods of extraction may include steam distillation, freeze distillation, alcohol distillation, hypersonic distillation, and CO2 distillation. Other embodiments may include other distillation or extraction methods as well as a combination of the methods previously mentioned. The formulations mentioned in the present disclosure are not limited by the extraction method used to obtain the essential oils.

Some embodiments use steam distillation, hypersonic distillation and CO2 distillation. The Ester/Alcohol Is removed and the specific Ester/Alcohol is used to make a mode of action response to the botanical. After this, the size is reduced to between 5 and 100 nanometers to allow better coverage. It is then encapsulated with Chitosan which not only allows better tank compatibility but increases the ability to enter into the plant and move. With the encapsulation, it allows us to code with time, pH and/or polarity which increases the contact and half-life.

Certain modes or mechanisms of action may be determined to produce given effects on the plants or the pests that come in contact with the plants. Certain compositions involve separating the composition into nanoparticles to provide a deeper intrusion into the plant or pest that comes in contact with the pest.

In the development of the disclosed embodiments, it has been observed that a certain amount of crosslinker agents are needed to ensure a true encapsulation of the given essential oil base. This was found to be for a simple time encapsulation as an example sodium triphosphate pentabasic (STP) was deemed a viable match. The use of STP between 3-10 g/l will derive the given chitosan load needed for a 0.1-2 percent weight per volume. Some embodiments may include the use of more crosslinker agents, and agents other than chitosan such as chitin, chitin-glucan, or other molecules containing similar functional groups.

In the development of the disclosed embodiments, it has been observed that internal and external nozzle cores are needed to spray the given oil during the microemulsion stage of the formulation. These allow microdroplets of oil to be suspended to create a true emulsion. Some other embodiments may include the use of Electrostatic adsorption or other electrochemical techniques to disperse particles in solution.

Observations of the experiments included an internal nozzle between 0.2-0.6 mm and an external nozzle between 0.7-1.0 mm forming an ability to make a true spherical copolymer encapsulation layer with a 24-hour decomposition breakdown.

In the development of the disclosed embodiments, it has been observed that modifications of cross-linker agents can be used to induce the copolymer encapsulation layer based on pH, time, or polarity. This is a key part of the present formulation as it enables users a multi-layer copolymer encapsulation by repeating the designed steps. Those individual layers can be coded the same of differently. Furthermore, the copolymer encapsulation layers can be further modified through the addition of hydrophilic molecules. This allows for increased hydrophilicity, improved stability, and enhanced drug delivery. Embodiments may include the use of chitosan or chitin as the hydrophilic crosslinking agents.

The disclosed formulation may be able to provide longer-lasting aromatics for perfumes, lotions, or other pharmaceutical-based needs. Formulations can also improve the efficacy for control of specific issues of agricultural needs by providing a coded material that can be delivered to the specific pH of an insect or disease limiting the environmental impact of non-selective insect death. In the soil, the half-life and ability of the given material to hold and perform reducing applications can be increased therefore reducing emissions and damaging issues.

Figure 1:
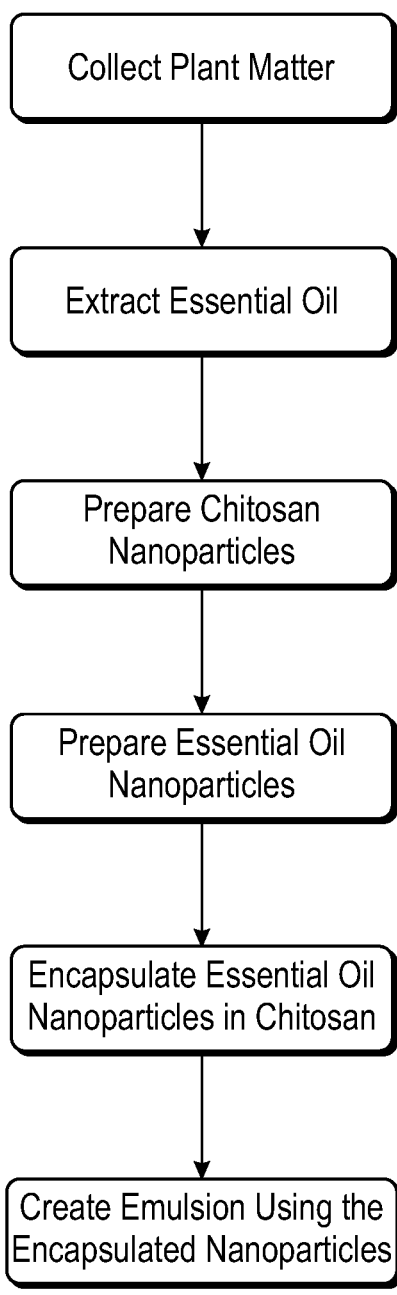
FIG. 1 is a flowchart showing the chitosan encapsulation of an active ingredient.

FIG. 1 is a flowchart showing the order of the collection and encapsulation of an active ingredient. First, plant matter is collected that contains the essential oil being used as the active ingredient, for example, if the active ingredient is cinnamon oil, the plant matter would be cinnamon. The essential oil is extracted from the plant matter. This is normally done by distillation, though other extraction methods are also possible. Nanoparticles of the chitosan and the essential oil are prepared. In some embodiments, the emulsion is created at this stage and a crosslinking agent is used to stabilize the chitosan. The chitosan nanoparticles and the essential oil nanoparticles are combined to form a stable emulsion. This emulsion may be contained in a container, bottle, or another vessel. In some embodiments, the emulsion may be manufactured and sold on a commercial scale. In some embodiment, the nanoparticles created may be small enough to enter an insect's spiracle organ and move to the air sac where the pesticidal compound may cause nerve and/or neurological damage.

In some embodiments, the essential oil is received from a third party that does the extraction. In a preferred embodiment, the chitosan is separated into polymeric nanoparticles. In some embodiments, the essential oil may be replaced with an extract.

In some embodiments, the process takes place in an aqueous solution. The water used in this solution may be H2O, dH2O, or ddH2O. The amount of water used may depend on the desired final concentration of the active ingredient. In some embodiments, the process takes place in another substance such as alcohol or oil. Some embodiments may also include the use of a filler, an extender, a wetting agent, a disintegrant, or a surfactant. These may be added at any time throughout the process.

Figure 2:
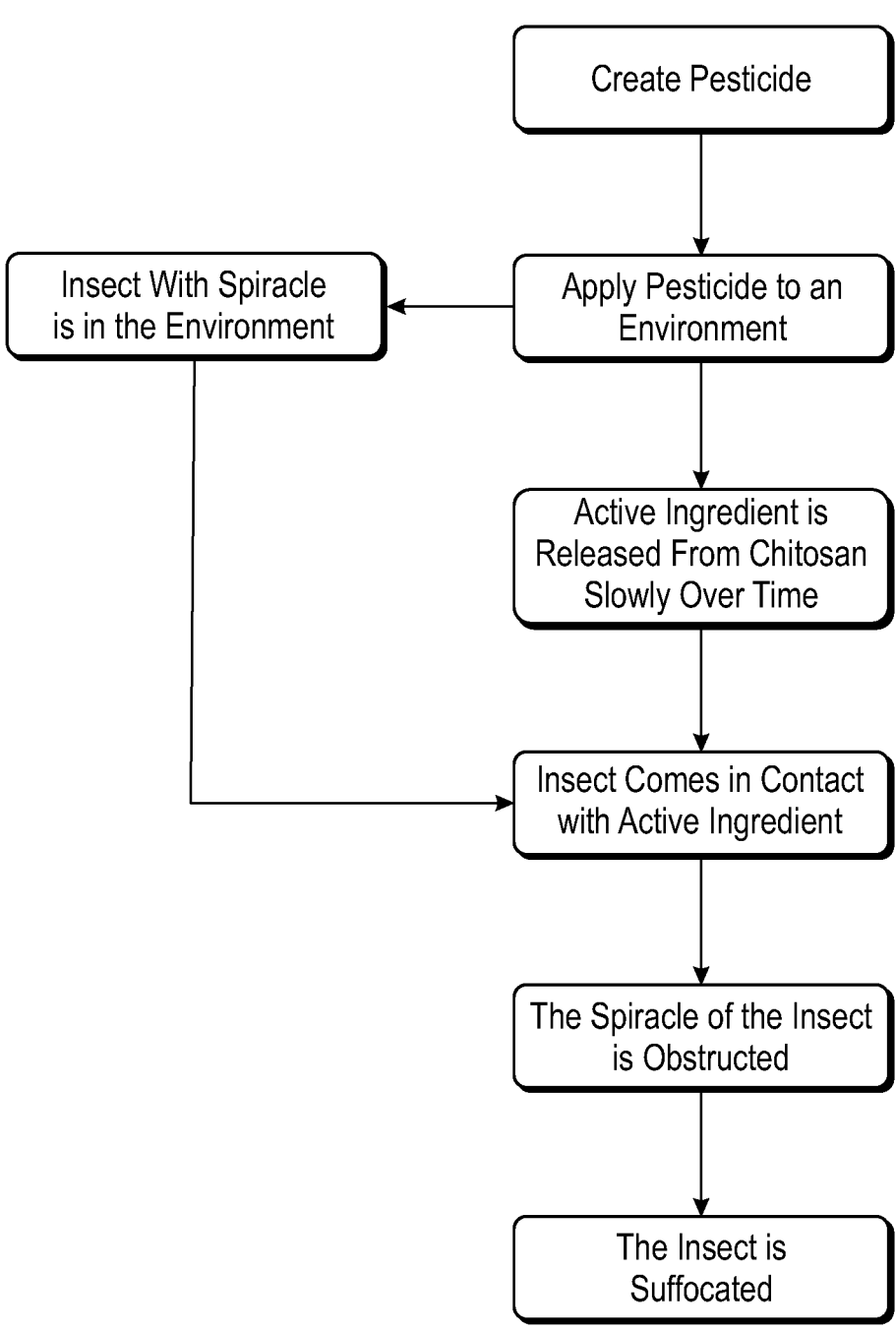
FIG. 2 is a flowchart illustrating the use of the pesticide on an insect with a spiracle organ.

FIG. 2 is a flowchart illustrating the use of the pesticide on an insect with a spiracle organ. The pesticide is created. In some embodiments, the creation of the pesticide may use the method in FIG. 1. The pesticide is applied to the environment, and the active ingredient (nanoparticles of essential oils/extract) is released slowly over time, an insect within the environment comes in contact with the active ingredients and the nanoparticles enter through the spiracle, obstructing the flow of air into the air sac of the insect. The insect suffocates from a lack of oxygen. In some embodiments, the insect suffocates due to paralysis instead of airflow blockage. In some embodiments, the environment is a field, lawn, wooded area, forest, jungle, swamp, body of water, house, or office. Other embodiments may also include other indoor or outdoor environments.

Figure 3:
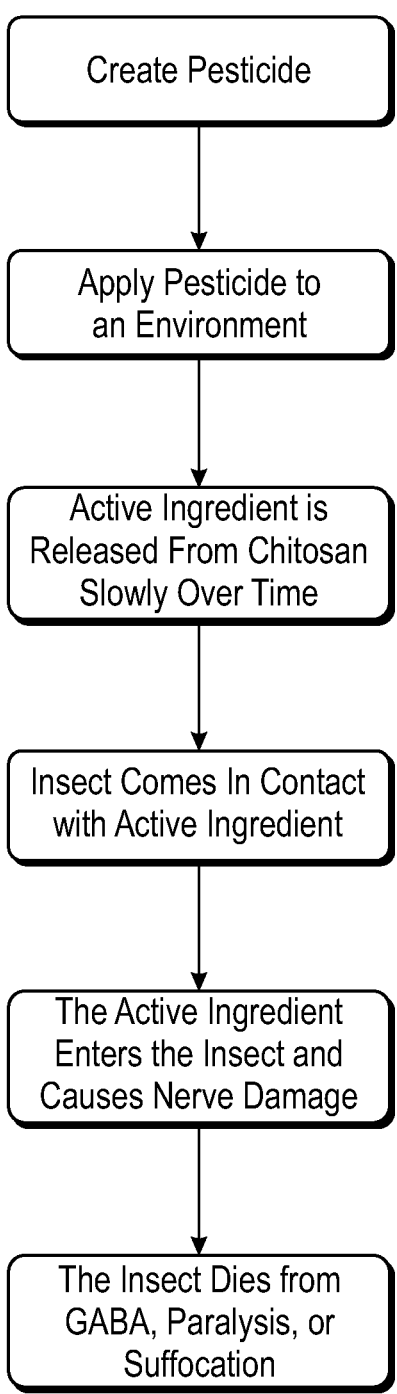
FIG. 3 is a flowchart showing possible modes of action used by the pesticide to kill an insect.

FIG. 3 is a flowchart showing possible modes of action used by the pesticide to kill an insect.

In some embodiments, volatile insecticides may enter through the spiracle and tracheal system. Pesticides may go in through the spiracle and cause other inhibitory effects (not only suffocation) such as inhibition of GABA receptors, paralysis, and other nerve effects. The pesticides enter with oxygen and go through the trachea to the air sac of the insect. This eventually causes nerve damage and can lead to full paralysis, brain damage, neural pathway damage, loss of appetite (starvation), and suffocation.

Figure 4:
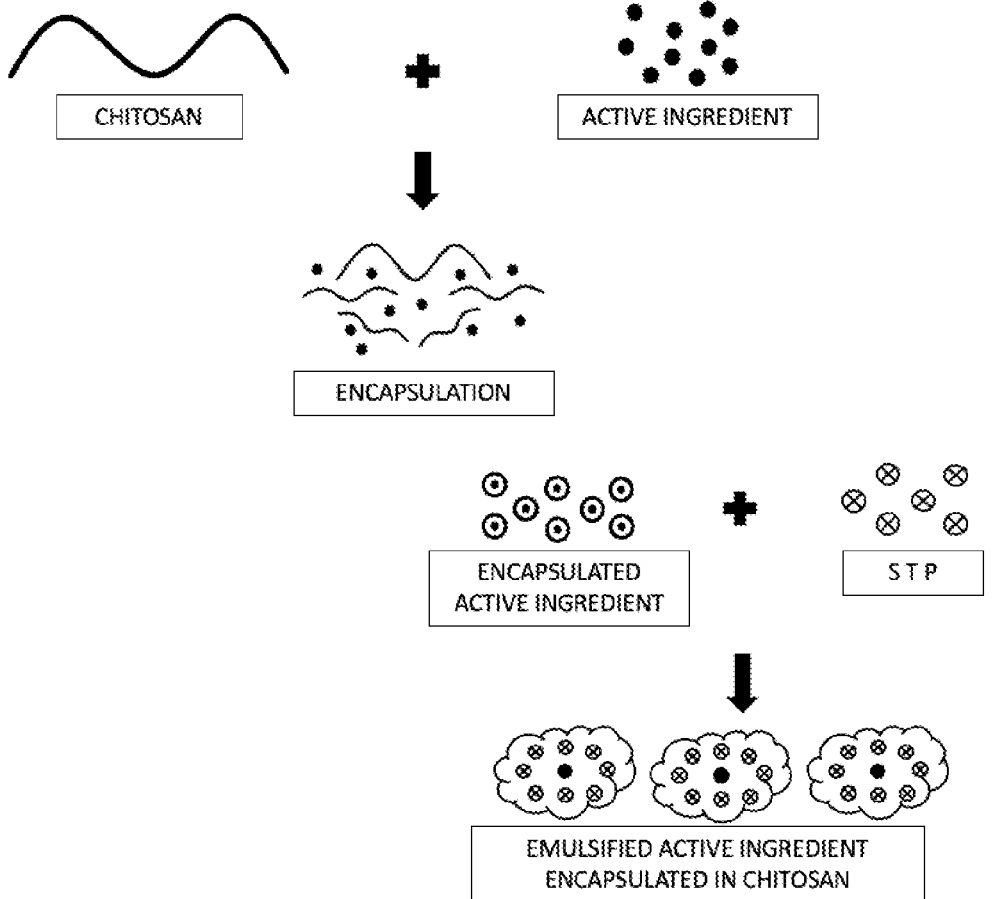
FIG. 4 is a diagram showing the chitosan encapsulation of an active ingredient.

FIG. 4 is a diagram showing the chitosan encapsulation of the active ingredient. In the first step, chitosan is combined with the active ingredient. The chemical structures of chitosan allow for the encapsulation of lipids/fat, terpenoid derivatives, and phenylpropanoid derivatives. These encapsulated compounds may be considered active ingredients. In preferred embodiments, the active ingredient is an essential oil/extract or naturally derived plant product such as geraniol, oxymatrine, or thyme extract. Once the chitosan and active ingredient are combined, the chitosan surrounds the active ingredient and shields it from outside forces. This allows for the slow release of the active ingredient into the environment based on the slow breakdown of the chitosan polymer.

In some embodiments, sodium tripolyphosphate (sodium triphosphate pentabasic (STP)) may be used as a crosslinking agent. This provides extra stability for the chitosan encapsulation, allowing it to have a longer shelf-life as a pesticide product.

In some embodiments, the STP-to-chitosan ratio may be changed to increase or decrease the stability of the chitosan encapsulation. This may allow for an increased shelf-life of the pesticide or a longer release of the active ingredients over time. In some embodiments, a less stable encapsulation may be desirable to enable a faster release of the active ingredient. In some cases the use of a cross linking agent is not necessary.

In some embodiments, the chitosan and active ingredient(s) are suspended in another liquid solution such as water or alcohol to create an emulsion. Some embodiments include the use of isopropyl alcohol.

In other embodiments, the composition may include an oil phase and an aqueous phase, wherein the oil phase includes one or more essential oils and the aqueous phase includes one or more active ingredients. The composition may further include a surfactant, a co-surfactant, and/or a wetting agent.

In other embodiments, plant essential oils are classified as plants' secondary metabolites and are, in general, complex mixtures of volatile and semi-volatile constituents. For instance, peppermint oil consists of several secondary metabolite constituents including menthol, menthone, methyl acetate, methofuran, isomenthone, germacrene-d, trans-sabinene hydrate and pulegone. The level of these constituents in the essential oils can vary based on the origin of the plants, the environmental conditions where the plants were grown, and the method that was used to obtain the essential oils.

Plant essential oils and their secondary metabolite constituents are readily obtained from plants utilizing simple processes including steam distillation, cold press, and solvent extraction. Some embodiments may also use alcohol extraction, CO2 extraction, and hypersonic extraction methods. These extraction processes and related science are applied to whole plant forms in large scale. Much of what is known from scientific studies about the pesticidal properties of these plant essential oils as contact toxicants is derived from analyses of their "whole plant" extracts. Some constituents of plant essential oils can also be obtained commercially in pure forms. One would understand that the extraction of oils on a smaller scale would have the same general effect when used in similar ratios and proportions.

While plant essential oils and their constituents (secondary metabolites) do not have a primary role in the metabolism of plants, they are valuable assets for plant defense, pollination, and communication. Plant secondary metabolites are organic compounds that are not directly involved in the normal growth, development or reproduction of plants. Most plant secondary metabolites have defensive roles and plants actively use them as signaling agents. Most plants are capable of responding to changes in their surroundings and can convey precise information about their overall health status through those responses. Scientific studies (Miresmailli et al. 2012) of plant-arthropod interactions within the field of chemical ecology have revealed highly specialized processes of controlled release of synthesized combinations of a plant's secondary metabolites.

These metabolites are either available as reservoirs in various parts of plants or synthesized de novo by plants when they need to use the metabolites to induce behavior or send a signal. Many studies have looked at how plants synthesize, store, utilize and control the release of their secondary metabolites to manipulate their environment (i.e. induce repellency and attractant effects on behavior of pests and their natural predators; defend their vital organs through chemical antifeedants, etc.) (Schoonhoven et al, 2006). Most plants are capable of responding to changes in their surroundings and can convey precise information about their overall health status through those responses (Volkov et al. 2003). As an example, some plants are capable of showing the footsteps of insects crawling on their foliage (Bowen et al. 2002), while some other plants react to pest oviposition or feeding (Kessler et al., 2001). One of the well-documented responses of plants to biotic stressors is the emission of herbivore-induced plant volatiles (HIPVs)—also known as info-chemicals (or semiochemicals) due to the fact that they carry some information about the status of the emitter. Plant semiochemicals (including plant secondary metabolites) can strongly affect the behavior of both predatory and herbivorous arthropods in nature and some plants are under strong selection pressure to release these volatiles. Various parts of plants, including leaves from both the abaxial and the adaxial side buds and roots, are known to emit HIPVs. The HIPVs are plant and pest-specific and the information they are conveying can change based on their composition and release rate.

When plants emit info-chemicals, they induce the desired action and behavior in the signal receiver. Some plants actively control the synthesis and release of these info-chemicals, both qualitatively and quantitatively. Many of the info-chemicals used in these plant communications are building blocks of plant essential oils (secondary metabolites). The same compounds that can trigger a behavior in one insect can kill another insect. Arthropods respond to specific mixtures of these volatile signals. Some plants are capable of actively changing the composition and release rate of their volatile chemical signals, and consequently changing the signal's intended message, and hence, the behavior or effect that is triggered.

Specific compositions and concentrations of botanical essential oil constituents (secondary metabolites) dictate the essential oil's specific attributes such as scent, taste, and viscosity as well as their pesticidal properties. Most of these constituents are the same low molecular weight chemicals as the volatile compounds that plants use for signaling and communication and, therefore, can easily volatilize out of the essential oils' matrix. Research performed by the inventors has shown that the presence of these constituents in a liquid mixture must be at certain levels for the efficacy of botanical essential oil-based pesticides to work as contact toxicants to control spider mites.

Some embodiments may use secondary metabolites such as flavonoids, tannins, saponins, steroids, glycosides, coumarins, anthraquinones, and alkaloids in place of their essential oil counterpart in any formulations present in this disclosure. For example, cinnamaldehyde may be used as an active ingredient in place of cinnamon oil in certain formulations.

The tendency of pesticides based on botanical essential oils to breakdown before their full toxic effect is achieved is a known limitation for their use in applications where the environmental conditions can accelerate the breakdown process or where their application is such that pests can avoid contact while the active ingredients remain toxic. The present invention has mitigated this limitation by concentrating on inhalation toxicity where the rate of secondary metabolite volatilization is controlled.

Many pests have detoxification mechanisms with which they can break down the toxins and avoid mortality. While essential oils-based botanical pesticides have the capability of knocking down pests after short periods of exposure, the challenge is to achieve mortality by sufficiently long exposures and or higher concentrations to overcome the pests' initial adaptive strategies.

Fumigants enter the arthropod pest body through inhalation. In this case, it is not necessary for pests to come into direct contact with the pesticide in liquid form as is the case with sprays and foggers that are contact pesticides. Liquid contact toxicants can be rendered ineffective if pests manage to avoid physical contact with the liquid pesticide. If a fumigant is used inside confined spaces, the pests cannot escape from the deadly effects of the toxins in gaseous form that eventually reaches them via the air they breathe. It is impossible for the pests to build immunity to the fumigant pesticide. Several essential oils have fumigant capabilities as a result of their volatilization properties against arthropod pests. During the course of developing improved apparatuses and methods of fumigation, the inventors have found that various secondary metabolites of essential oils volatilize from the essential oil mixture at different rates. Heretofore unknown and unexpected is the ability to control differential volatilization rates of individual secondary metabolite constituents of botanical essential oils for use as fumigant pesticides, as opposed to controlling the breakdown rate of the essential oils as a liquid mixture when such mixtures are used as contact pesticides.

Some embodiments are related to controlling volatilization rates and composition of secondary metabolite constituents of botanical essential oil-based pesticides in the air to achieve the durational toxicity and concentration needed for complete mortality of target pests in contained spaces and a very effective repellant where the space is not sufficiently contained.

In some other embodiments, the composition may include an oil phase and an aqueous phase, wherein the oil phase includes one or more essential oils and the aqueous phase includes one or more active ingredients. The composition may further include a surfactant, a co-surfactant, and/or a wetting agent.

The composition may include an essential oil and a carrier oil. The essential oil is selected from the group consisting of *eucalyptus* oil, cinnamon oil, peppermint oil, lemongrass oil, rosemary oil, clove oil, and thyme oil. The carrier oil is selected from the group consisting of olive oil, coconut oil, jojoba oil, and almond oil.

The essential oils are encapsulated in a water-soluble polymer. The polymer is then mixed with water to create a slurry. The slurry is then sprayed onto the desired surface. The composition comprises: a) an oil phase, b) a surfactant, and c) a cosurfactant.

In some embodiments, the composition for may include purest form of chitosan.

Chitosan is a natural biopolymer that has shown to be effective in protecting crops from fungal infections. Citric acid is a natural preservative and has antifungal properties. Clove oil is an essential oil with insecticidal, fungicidal and nematicidal properties.

Chitosan, derived from the exoskeletons of shrimp, crab, and other shellfish, has been shown to increase the efficacy of essential oils when used as a co-formulant and can be used in a variety of ways including as a soil drench, foliar spray, or as a seed treatment.

Chitin and chitosan are naturally-occurring compounds that have potential in agriculture with regard to controlling plant diseases. These molecules were shown to display toxicity and inhibit fungal growth and development. They were reported to be active against viruses, bacteria, and other pests. Fragments from chitin and chitosan are known to have eliciting activities leading to a variety of defense responses in host plants in response to microbial infections, including the accumulation of phytoalexins, pathogen-related (PR) proteins and proteinase inhibitors, lignin synthesis, and callose formation. Based on these and other proprieties that help strengthen host plant defenses, interest has been growing in using them in agricultural systems to reduce the negative impact of diseases on yield and quality of crops.

One purpose of the chitosan capsulation is that you can wrap into mined layers allowing for them to work over a period. This also works on a secondary aspect of being safe for humans allowing for the mosquito materials to be blended into lotions and or sun tanning materials. With this they lock into Dermis layer of the skin allowing for longer water stability. This will give us the ability to last up to 20 hours even after swimming for repelling mosquitos.

The use of Pyroligneous Acid in the formulations at up to a 1.5-6% may be added to increase microbial and insecticidal activities. This also aids in plant health after control of insects and diseases. Some embodiments may include the use of chitosan encapsulation of the Pyroligneous Acid to allow longer-lasting effectiveness of the active ingredient in the formulation.

Certain embodiments include focusing on biological-based formulations instead of botanical formulations. Certain embodiments will be looking at formulations using more botanical-based materials and also looking at blending botanical and bacteria, mycorrhizal, and fungi to allow a coexisting formulation allowing for contact and longer systemic control. Some embodiments also look at coding the encapsulation allowing us to kill specific insects or diseases as well as increase the half-life of the products. Using mechanisms of action to determine active ingredients effect may also be used in experimentation.

Certain embodiments may also pertain to emulsion-in-water (EW) formulations.

A novel approach is the use of a specific ester to enhance a specific mode of action and combine multiple modes into a single bottle. Then encapsulate the material allowing for a longer lifespan of the material, reducing environmental controls and increase the efficacy of the formulation. This also allows the material to be added to or impregnated into netting, sprayed on walls to support WHO. These pesticides may have use cases other than for agriculture (such as removing ants from a house).

Again, we do model extractions not whole plant extractions allowing for cleaner materials. Some embodiments do absolutes not essentials as those are heavy in alcohol and this eliminates this allowing for superior control and then chitosan encapsulation allows the embodiment to also be NOP compliant allowing for absorption into the plant by CERK1. Some embodiments may include the use of cold-pressed citrus oil to help with penetration of the formulation into the plant or into the pest. This citrus oil mad be acquired by methods other than cold-pressing. In some embodiments, this material or compound can also be impregnated into a base allowing for seed coating and can be mixed with additional supportive materials to establish seeds as well. This may help to establish a higher germination rate while still accounting for pesticidal activities.

More specifically, some embodiments are directed to providing a delivery method of essential and natural oils to insects or other pests alike which in turn exhibits highly effective control mechanism without causing plant or human phytotoxicity.

In some embodiments, the composition and formulation disclosed targets and inhibits the functions of the sensors or/and the spiracle of the pest, forming a coating or a barrier around the pest body surface, more particularity blocking the breathing spiracles, sensory hairs and organs of the pest. Spiracles are openings on the thorax of hexapods, including insects. The spiracles open into chitinous tubes called tracheae which then further subdivide until becoming less than 1 mm in diameter tracheoles, forming a network all through the body of the organism, said network is the respiratory system of these organisms.

The spiracles are muscular valves in the insect body, and their opening can be controlled, mostly in order to regulate water loss. This mechanism is controlled by the central nervous system but can also react to localized chemical stimuli. Several aquatic insects have similar or alternative closing methods to prevent water from entering the trachea. The timing and duration of spiracle closures can affect the respiratory rates of the organism.

In some embodiments, air enters the insect's body through valve-like openings in the exoskeleton. These openings (called spiracles) are located laterally along the thorax and abdomen of most insects usually one pair of spiracles per body segment. Airflow is regulated by small muscles that operate one or two flap-like valves within each spiracle-contracting to close the spiracle, or relaxing to open it.

The phospholipids of the composition provide a first layer that blocks the respiratory system of the pest and further inhibits the pest's nervous system from environmental stimuli.

The composition of the disclosed embodiments targets the spiracles that act as muscular valves in some pests, leading to the internal respiratory system, a densely networked array of tubes called tracheae. This network of transverse and longitudinal tracheae equalizes pressure throughout the system. The composition is formulated as contact pesticides that penetrate the pest cuticle or enter through the spiracles of the respiratory system. Some embodiments may block these valves using an oil-based emulsion to block air from getting to the respiratory system and suffocate the pest.

The composition of disclosed embodiments is an aqueous preparation which may be in the form of a liquid, solution, lotion, mixture, compound, formulation, gel, cream, liquid infusion, spray, suspension, emulsion, emollient preparation, emollient moisturizer and any combination thereof.

It is further classified to invertebrate pests' species, plant pests' species, and vertebrate pests' species. Some of the embodiments may feature a composition that comprises of a combination of organo-metalloid complex and a phospholipid compound. This combination is a mixture of: boro-glycerin complex in a range of about 65% by weight, EDTA in a range of about 0.5% by weight. 0.5% SLS, about 2% Magnesium sulfate, about 15% lecithin, about 7% paraffin wax, about 7% isopropanol, about 2% dextrose monohydrate and about 1% aromatic oil with concentration of about 2.5%.

Some embodiments are a combination of organo-metalloid complex and a phospholipid compound. This combination is a mixture of citric acid and glycerin complex in a range of about 65% by weight, EDTA in a range of about 0.5% by weight, 0.5% SLS, about 2% potassium permanganate, about 15% lecithin, about 7% paraffin wax, about 7% isopropanol, about 2% dextrose monohydrate, and about 1% aromatic oil with concentration of about 2.5%.

The inorganic salts magnesium sulfate, calcium chloride or potassium permanganate can be used interchangeably in the above compositions.

In other embodiments, the detergent SLS combined with boro-glycerin enables the adherence of the coating formation to the pest respiratory system. Since the pest body is covered with a hydrophobic fraction there is an improved adsorption of the boro-glycerin around the pest body whilst the lecithin and SLS as a mixture provides a binding substance which allows conjugation between the hydrophobic fraction to the hydrophilic fraction. This results in a higher entropic state which causes non-polar molecules to clump together to reduce the surface area exposed to water and decrease the entropy of the system.

In other embodiment, the phospholipids e.g. lecithin when mixed with SLS forms micelles in an aqueous environment. The micelles target the cuticle of the pest thereby, forming a coated barrier around the pest body.

In other embodiments, the Magnesium sulfate salt or Potassium permanganate is a hygroscopic material which enables the boro-glycerin complex comprising boric acid compound to be dissolved and provides an improved pesticide with low toxicity to the environment.

In other embodiments, the glycerin is used as a solvent medium of the composition for dissolving and to be reacted with the boric acid forming a boro-glycerine complex. Thereby about 20 to 30% boric acid compound is mixed at 25° C. with about 70 to 80% of glycerin forming a boro-glycerine complex In other embodiments of the present invention, the composition has low viscosity resulting from the alcohol compound.

Some embodiments are related to a pest control composition comprising a coating composition, wherein said composition comprises a combination of an organo-metalloid complex and a phospholipid compound. In some embodiments, the said composition is aqueous.

In some embodiments, aerosol administration is dispersible upon the pest body surface.

In some embodiments, the organo-metalloid complex comprises a mixture of a boro-glycerin complex in a range of about 65% by weight and aminopolycarboxylic acid compound in a range of about 0.5% by weight.

Some embodiments are related to a pest control composition comprises a combination of an organo-metalloid complex and a phospholipid compound, wherein said organo-metalloid complex is a mixture of citric acid-glycerin in a range of about 65% by weight and an aminopolycarboxylic acid compound in a range of about 0.5% by weight.

In some embodiments, a combination of the boro-glycerin complex and the aminopolycarboxylic compound in a predefined ratio is further configured to disrupt spiracle control in said pests, further increasing mortality of said pests.

In some embodiments, the citro-glycerin complex and aminopolycarboxylic compound in a predefined ratio further configured to disrupting spiracle control in said pests, further increasing mortality of said pests.

In some embodiments, the glycerin is configured to dissolve and to be reacted with the boric acid further configured to form a boro-glycerine complex.

In some embodiments, the disclosed composition is about 25% boric acid compound is mixed at 25° C. with about 75% of glycerin further configured to form a boro-glycerine complex In some embodiments, the glycerin is configured to dissolve and to be reacted with the citric acid further configured to form a citro-glycerine complex.

In some embodiments, the disclosed composition is about 25% citric acid compound is mixed at 25° C. with about 75% of glycerin further configured to form a citro-glycerine complex.

In some embodiments, the glycerin (or glycerol) may be synthetically derived from soap or biodiesel manufacturing as a by-product. Other embodiments include the production of naturally derived glycerin found in plants, yeast fermentation, steam hydrolysis, or other non-synthetic processes. In some embodiments that include organic farming, naturally-derived glycerin may need to be used. Synthetically derived glycerin is not allowed in commercial organic farming, so some embodiments may only concern the use of naturally-derived glycerin. Other embodiments may use synthetically derived glycerin to save money on the production of non-organic products.

In some embodiments, phospholipid compound comprises at least one substance selected from the group consisting of Phosphatidic acid (phosphatidate), Phosphatidylethanolamine (cephalin) (PE), Phosphatidylcholine (lecithin) (PC), Phosphatidylserine (PS), Phosphatidylinositol (PI), Phosphatidylinositol phosphate (PIP), Phosphatidylinositol bisphosphate (PIP2), Phosphatidylinositol triphosphate (PIP3), Ceramide phosphorylcholine (Sphingomyelin) (SPH), Ceramide phosphorylethanolamine (Sphingomyelin) (Cer-PE), Ceramide phosphoryllipid and any combination thereof.

In some embodiments, the composition comprises at least one substance selected from the group consisting of a detergent, paraffin wax, aromatic oil, phospholipid, alcohol, dextrose monohydrate, inorganic salts selected from a group consisting of magnesium sulfate, potassium permanganate calcium chloride, and any mixture thereof.

In some embodiments, phospholipids when mixed with SLS forms micelles in an aqueous environment; said micelles are dispersible on the cuticle of a pest forming at least one layer around on said pest cuticle.

In some embodiments, the composition dispersed on a pest provides a thin coating layer upon the epicuticle of the pests for inhibition of pest host sensing.

In some embodiments, the composition is configured to impair respiration of the pest, forming a barrier upon at least one selected from the group consisting of the pest body surface, the breathing spiracles, the sensory hairs and organs.

In some embodiments, the composition when layered on a cockroach in vivo and in contact with a substance selected from a group consisting water, moisture, humidity, and any combination thereof, facilitates entry of water via dysfunctional spiracles, into said insect, sufficient to kill said pest.

In some embodiments, said aqueous preparation may take the form of a liquid, solution, lotion, mixture, compound, formulation, gel, cream, liquid infusion, spray, suspension, emulsion, emollient preparation, emollient moisturizer and any combination thereof.

In some embodiments, the composition mentioned above, additionally comprising at least one substance selected from the group consisting of about 0.5% detergent, about 15% phospholipid compound, about 7% alcohol, about 1% aromatic oil with concentration of about 2.5%, about 7% paraffin wax, about 2% dextrose monohydrate, about 1% aromatic oil and about 2% inorganic salt selected from a group consisting magnesium sulfate, calcium chloride or potassium permanganate, and any mixture thereof.

Some embodiments are related to a dispersing device for delivering an aerosolized spray of composition, comprising: a housing having an internal cavity containing said pest control composition; and a control valve for delivering said composition from the cavity to a selected site; wherein the composition of claim 1 comprises said mixture of boro-glycerin complex or said mixture of citric acid-glycerin complex.

Some embodiments are related to a method for controlling pests comprising steps of providing a coating composition, and applying said composition to a location to be so controlled wherein said composition comprises a combination of organo-metalloid complex and a phospholipid compound. Reference is now made to an embodiment of the present invention disclosing the method mentioned above, wherein said composition is aqueous. In some other embodiments, dispersion of said composition may be applied upon the pest body surface directly or indirectly.

In some other embodiments, the composition may additionally comprise of organo-metalloid complex mixture of boro-glycerin complex in a range of about 65% by weight and aminopolycarboxylic acid compound in a range of about 0.5% by weight.

Some embodiments are related to a method for controlling pests comprising steps of providing a combination of organo-metalloid complex and a phospholipid compound, wherein said organo-metalloid complex is a mixture of citric acid-glycerin in a range of about 65% by weight and aminopolycarboxylic acid compound in a range of about 0.5% by weight.

Some embodiments are related to the method mentioned above, wherein about 25% boric acid compound is mixed at 25° C. with about 75% of glycerin further forming a boro-glycerine complex.

Reference is now made to an embodiment of the present invention disclosing the method mentioned above, wherein the glycerin is dissolving further reacting with the citric acid further forming a citro-glycerine complex.

Reference is now made to an embodiment of the present invention disclosing the method mentioned above, wherein about 25% citric acid compound is mixed at 25° C. with about 75% of glycerin further forming a citro-glycerine complex.

In some other embodiments, compositions may additionally comprise of at least one substance selected from the group consisting of Phosphatidic acid (phosphatidate), Phosphatidylethanolamine (cephalin) (PE), Phosphatidylcholine (lecithin) (PC), Phosphatidylserine (PS), Phosphatidylinositol (PI), Phosphatidylinositol phosphate (PIP), Phosphatidylinositol bisphosphate (PIP2), Phosphatidylinositol triphosphate (PIP3), Ceramide phosphorylcholine (Sphingomyelin) (SPH), Ceramide phosphorylethanolamine (Sphingomyelin) (Cer-PE), Ceramide phosphoryllipid and any combination thereof.

In some other embodiments, compositions may additionally comprise of at least one substance selected from the group consisting of a detergent, paraffin wax, phospholipid, aromatic oil, alcohol, dextrose monohydrate, inorganic salts selected from a group consisting of magnesium sulfate, potassium permanganate calcium chloride, and any mixture thereof.

The present pesticides are deemed safe for vertebrates because they are derived from natural sources and are designed to target specific pests, thus minimizing exposure to non-target species. They are biodegradable, meaning they break down quickly in the environment and do not leave long-lasting residue of active ingredients. In some embodiments, chitosan, another naturally derived is used to encapsulate the active ingredients to slow the release over time into the environment.

Another reason that pesticides are safe for vertebrates is that they are subject to strict regulation by government agencies such as the Environmental Protection Agency (EPA) in the United States. The EPA thoroughly evaluates the potential impacts of pesticides on a wide range of species, including vertebrates, before they are approved for use. This process includes extensive testing to determine the potential toxicity of the pesticide and the likelihood of exposure to non-target species.

Additionally, many studies have been conducted on the impacts of pesticides on vertebrates, and the results have consistently shown that when used according to label instructions, the risks to vertebrates are low. For example, research on birds has found that exposure to organic pesticides does not significantly impact population numbers or reproductive success. Similarly, studies on mammals have found that exposure to organic pesticides does not cause significant harm to individuals or populations.

In preferred embodiments, the active ingredients used do not affect crops, livestock, humans, or other animals in meaningful ways. Some embodiments include the use of nanoparticles of active ingredients to allow for active ingredients to enter an insect's spiracle and eventually go to their air sac. This may cause nerve damage to the insect causing inhibition of GABA receptors, paralysis, loss of appetite, or other nerve and neuron damage.

In some embodiments, volatile insecticides may enter through the spiracle and tracheal system. Pesticides may go in through the spiracle and cause other inhibitory effects (not only suffocation). GABA, paralysis, other nerve effects. The pesticides enter with oxygen and go through the trachea to the air sac of the insect. This eventually causes nerve damage and can lead to full paralysis, brain damage, neural pathway damage, loss of appetite (starvation), and suffocation.

III. PRODUCTION AND DISTILLATION OF ESSENTIAL OILS

Some embodiments may include the production of essential oils and essential extracts. Plant essential oils and extracts are classified as secondary metabolites and are, in general, complex mixtures of volatile and/or semi-volatile constituents. This allows them to be removed/extracted from plant matter through a process using distillation methods such as alcohol extraction, solvent (such as benzene or hexane) extraction, hot-water extraction, hypersonic distillation, CO2 distillation, supercritical CO2 extraction, cold-water extraction, cold compression (expression), steam distillation, vacuum distillation, cold pressing, percolation/hydrodiffusion, fractional distillation, Enfleurage, Some embodiments use steam distillation (or low-pressure steam distillation) to extract essential oils from plant matter. Steam distillation is a process used to separate the volatile components of a mixture, typically by boiling the mixture and condensing the steam. In the case of low-pressure steam distillation, the steam is generated at low pressure which allows for the separation of components with lower boiling points. The low-pressure steam also helps to preserve the delicate aroma and flavor compounds of the plant material. These aromatic compounds may serve as a repellant against certain insects, so keeping them in-tact may be beneficial in some embodiments. The steam passes through the plant material, causing the volatile components to evaporate and become dissolved in the steam. The steam is then condensed, allowing the separated essential oil to be collected. The remaining water can be discarded or used as a hydrosol, a byproduct of steam distillation that contains water-soluble components of the plant material. The water may be separated easily because of the difference in polarity of the substances. Some embodiments may include a separate vessel for creating steam under the plant material without boiling the plant material in water during the distillation process. Some embodiments may include the use of hydrodiffusion or percolation.

Some embodiments may include the use of vacuum distillation during the extraction process. Vacuum distillation is a process used to separate the components of a mixture based on their boiling points. It is similar to traditional distillation methods (such as steam distillation), but it takes place under reduced pressure, which lowers the boiling points of the components and allows them to be separated at lower temperatures. This reduces the risk of thermal degradation of heat-sensitive components (such as the aromatic compounds found in plant matter). This allows for a highly concentrated substance that may be produced without using water in the distillation process (the end product is not diluted). Other embodiments may use fractional distillation which is a similar process that uses more heat at normal atmospheric pressure. Some embodiments may include the use of a packed column to get a more concentrated extract, or the use of an unpacked column for a faster distillation process.

Cold pressing may also be used do extract the oils, particularly citrus fruits, such as oranges, lemons, and grapefruits, which have a high oil content and a relatively low viscosity. Cold pressing is a method used to extract essential oils from plant material without the use of heat or solvents. In this process, the plant material is mechanically pressed to release the essential oil, which is then separated from the plant material using a separator, such as a centrifuge. The resulting oil is considered a "cold-pressed" essential oil and is valued for its natural fragrance, flavor, and beneficial properties. Cold pressing is typically used for The process typically involves cutting the fruit in half and then pressing the juice and essential oil from the fruit. The essential oil rises to the surface of the juice, and in some embodiments, may be separated using a centrifuge. Some embodiments may include pressing the fruits and then using distillation methods to separate the oil from the pressed juice.

Supercritical carbon dioxide extraction may also be used for extracting essential oils from plant matter. Volatile oils, aldehydes, and ketones are easily soluble in liquid $CO_2$. This CO2 may then be heated to room temperature and moved to normal atmospheric pressure to remove the CO2 from the volatile oils.

In some embodiments, solvent (alcohol or benzene) extraction (or liquid-liquid extraction) may also be used to extract the essential oils from the plant matter. Some embodiments may also use enfleurage.

Some embodiments may include the extraction of oleoresins from plant matter, which include the volatile oils and resins from certain plants. In some embodiments, these oleoresins may also be used as active ingredients in certain pesticides and repellants.

IV. CONTROLLING NEMATODES

Some embodiments are related to a formulation for controlling plant-parasitic nematodes that contains geraniol at a concentration of 500 to 4,000 ppm, derived from natural substances and is found to be environmentally friendly per the EPA under FIFRA 25(b), and in turn, exhibits highly effective nematocidal control mechanisms without causing plant phytotoxicity.

Some embodiments are configured to provide a safe and naturally derived material having nematocidal activity.

Extraction of main anatomic parts to establish a purer form of the botanical. A clean oxymatrine molecule may be used to increase efficacy. Cleaner and purer oils and ingredients may allow for a reduced load of active ingredients. Also, without formulations, the volatility of the oil itself is removed and wrapped with Chitosan. Some embodiments use steam distillation, or use CO2 and Hypersonic distillation plus multiple different absolutes are coded allowing for 4-5 modes of action from GABA to paralysis. Unlike others including EcoWin who use one specific extraction base. Other mechanisms or modes of action may be used in the formulation of pesticides or in the production of essential oils/botanicals.

In disclosed embodiments, the plant-parasitic nematodes may be demonstrated by root-knot nematodes, root-lesion nematodes, spiral nematodes, cyst nematodes, and multiple other plant parasitic nematodes.

Root-knot nematodes infest thousands of different plant species including vegetables, fruits, and row crops. Cyst nematodes are known to infest tobacco, cereals, sugar beets, potato, rice, corn, soybeans, and many other crops. *Heterodera schachtii* (BCN) principally attacks sugar beets, and *Heterodera avenae* is a pest of cereals. *Heterodera zeae* feeds on corn, and *Globodera rostochiensis* and *G. pallida* feed on potatoes. The soybean cyst nematode (SCN) is present in every soybean-producing state in the US, and causes total soybean yield losses estimated to be nearly $1 billion per year. Once SCN is present in a field, it cannot feasibly be eradicated using known methods. Although soybean is the major economic crop attacked by SCN, SCN attacks some fifty hosts in total, including field crops, vegetables, ornamentals, and weeds.

Tea tree oil root-knot nematode (RKN) is a destructive nematode, which forms galls on the roots of tea tree oil plants. The causative agent is *Meloidogyne incognita* (Kofoid and White) Chitwood, a nematode that can infest a variety of plant species. Nutrient and water uptake are decreased in infested plants, and plants may become susceptible to pathogens, especially *Fusarium* wilt. Consequently, yield is decreased in plants infested with RKN. In the US alone, an estimated 10.93% of tea tree oil yield loss in 2004 was attributed to RKN which is widespread throughout the U.S. Tea tree oil Belt. Methods to mitigate RKN damage include rotating tea tree oil crops with non-susceptible crops and application of costly nematicides. However, the most effective way for tea tree oil growers to reduce yield loss and crop damage due to RKN is to grow RKN resistant tea tree oil cultivars.

Seven types of plant-derived biological materials and twelve plant extracts were assessed for nematocidal activity in the development of disclosed embodiments.

In the development of disclosed embodiments, nematocidal activity on root-knot nematodes (*Meloidogyne* spp.) was assessed using geraniol, azadirachtin, clove oil, oregano oil, pyrethrin, oxymatrine, neem extract, *Ostericum koreanum* extract, clove extract, *Myristica fragrans* extract, *Acorus gramineus* extract, *Kaempferia galanga* extract, and *Amomum cardamomum* L. extract. Based on the results, superior nematocidal activity was confirmed when geraniol was utilized alone or in combination with oxymatrine, neem extract, clove extract, or *Ostericum koreanum* extract.

In particular, when geraniol was used at 500 to 4,000 ppm, superior nematocidal control was demonstrated without plant phytotoxicity. Still, plant phytotoxicity was shown to occur upon treatment with geraniol at 4,500 ppm or more.

Therefore, some embodiments are related to a formulation for controlling plant-parasitic nematodes containing geraniol at a concentration of 50 to 4,000 ppm.

Geraniol is monoterpene alcohol contained in plant essential oil and can be utilized without constraint as to the source plant. Geraniol also has low mammalian toxicity and is biodegradable.

In some embodiments, the nematocidal activity may become insignificant if the quantity of geraniol in the composition for controlling plant-parasitic nematodes is less than 50 ppm. On the other hand, if the amount exceeds 4,500 ppm, phytotoxicity may be caused in crops.

Signs of nematode damage include stunting and yellowing of leaves, as well as wilting of the plants during hot periods. However, nematodes, including SCN, can cause significant yield loss without obvious above-ground symptoms. For example, an infestation of SCN to a plant can result in dwarfed or stunted roots, decrease the number of nitrogen-fixing nodules on the roots, and/or make the roots more susceptible to attack by other soil-borne plant pests or pathogens.

In some embodiments, the formulation for controlling plant-parasitic nematodes may exhibit superior nematocidal activity even when containing geraniol alone. To demonstrate a higher and more stable nematocidal efficiency, a plant extract selected from the group consisting of an oxymatrine, neem extract, an *Ostericum koreanum* extract, and a clove extract may be added. Here, the volume ratio of the plant extract and the geraniol is preferably 3:1 to 6:1 based on the same concentration. If the volume ratio of the plant extract and the geraniol falls out of the above range, there is a concern that phytotoxicity may occur.

In some embodiments, the nematocidal activity may become insignificant if the quantity of geraniol in the composition for controlling plant-parasitic nematodes is less than 50 ppm. On the other hand, if the amount exceeds 4,500 ppm, phytotoxicity may be caused in crops.

The plant extracts may be acquired using a process selected from the group consisting of typically known extraction processes, such as alcohol extraction, hexane extraction, hot-water extraction, hypersonic distillation, CO2 distillation, cold-water extraction, cold compression (expression), and steam distillation.

Some embodiments are directed to a formulation for controlling plant-parasitic nematodes, including the formulation for controlling plant-parasitic nematodes as an active ingredient, and to a method of controlling plant-parasitic nematodes including controlling nematodes using the composition for controlling plant-parasitic nematodes.

Here, the crops to be treated may include all known crops, and the formula may be delivered directly, delivered to the roots, the soil, leaves, or other areas of the plant. This provides methods of reduction to the loss of billions in agricultural revenue and production losses annually.

Seven types of plant-derived biological materials and twelve plant extracts were assessed for nematocidal activity in the development of disclosed embodiments.

In the development of disclosed embodiments, nematocidal activity on root-knot nematodes (*Meloidogyne* spp.) was assessed using geraniol, azadirachtin, clove oil, oregano oil, pyrethrin, oxymatrine, neem extract, *Ostericum koreanum* extract, clove extract, *Myristica fragrans* extract, *Acorus gramineus* extract, *Kaempferia galanga* extract, and *Amomum cardamomum* L. extract. Based on the results, superior nematocidal activity was confirmed when geraniol was utilized alone or in combination with an oxymatrine, neem extract, clove extract, or *Ostericum koreanum* extract. In particular, when geraniol was used at 500 to 4,000 ppm, superior nematocidal control was demonstrated without plant phytotoxicity. Still, plant phytotoxicity was shown to occur upon treatment with geraniol at 4,500 ppm or more.

Therefore, an aspect of the current invention pertains to a formulation for controlling plant-parasitic nematodes containing geraniol at a concentration of 50 to 4,000 ppm.

The mode of action of the composition is to act as an irritant to the insect, causing it to stop feeding. The composition may also kill the insect by suffocation.

Some embodiments include specific modes of action used by the pesticidal active ingredients in the formulation, the modes of action may be membrane disruption, substrate deprivation, binding to cell wall complexes, enzyme inactivation, GABA inhibition, acetylcholine inhibition, paralysis, protein binding, inactivation of disulfide bridges, or interaction with eucaryotic DNA.

To increase efficacy, the composition may be heated to just below the boiling point of the essential oils. This specific technique makes the oils more volatile and easier to inhale by the pests.

This composition is designed to be used as an insecticide, fungicide, nematicide, and larvicide. The composition includes one of oxymatrine, sephora pachycapra, neem oil, clove, and Geraniol. This composition is used to control plant pests and is safer and more effective than other pesticides. The composition is also effective against nematodes and may help to prevent soil pollution.

Geraniol is a monoterpene alcohol contained in plant essential oil and can be utilized without constraint as to the source plant.

In the present invention, the nematocidal activity may become insignificant if the quantity of geraniol in the composition for controlling plant-parasitic nematodes is less than 50 ppm. On the other hand, if the amount exceeds 4,500 ppm, phytotoxicity may be caused in crops.

According to the present invention, the formulation for controlling plant-parasitic nematodes may exhibit superior nematocidal activity even when containing geraniol alone.

To demonstrate a higher and more stable nematocidal efficiency, a plant extract selected from the group consisting of an oxymatrine, neem extract, an *Ostericum koreanum* extract, and a clove extract may be added. Here, the volume ratio of the plant extract and the geraniol is preferably 3:1 to 6:1 based on the same concentration.

If the volume ratio of the plant extract and the geraniol falls out of the above range, there is a concern that phytotoxicity may occur.

The plant extracts may be acquired using a process selected from the group consisting of typically known extraction processes, such as alcohol extraction, hexane extraction, hot-water extraction, hypersonic distillation, $CO_2$ distillation, cold-water extraction, cold compression (expression), and steam distillation.

In the present invention, the plant-parasitic nematodes may be demonstrated by root-knot nematodes, root-lesion nematodes, spiral nematodes, cyst nematodes, and multiple other plant parasitic nematodes In the present invention, the composition for controlling plant-parasitic nematodes may be used alone but is not particularly limited to that and may additionally include a suitable diluent or excipient depending on the dosage form or use purposes formulation.

As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some embodiments pertain to a formulation for controlling plant-parasitic nematodes, including the formulation for controlling plant-parasitic nematodes as an active ingredient, and to a method of controlling plant-parasitic nematodes including controlling nematodes using the composition for controlling plant-parasitic nematodes.

Some embodiments may also comprise a nematicide (or pesticide) comprising the use of *Quillaja saponaria Molina* (Soapbark). Some embodiments may include *Quillaja saponaria Molina* nano encapsulated in chitosan as an active ingredient for the anti-nematode formulation.

Another embodiment may comprise a composition for controlling various species of plant-parasitic nematodes, containing geraniol at a concentration of 50-4000 ppm in addition to *Quillaja saponaria Molina* in a ratio of about 1:1 with the geraniol. The nematodes may pertain to one selected from the group consisting of a root-knot nematode, cyst nematode, root-lesion nematode, burrowing nematode, dagger nematode, and spiral nematode. This formulation may contain *Quillaja saponaria Molina* and geraniol as active ingredients.

The present invention provides a formulation for controlling plant-parasitic nematodes containing geraniol at a concentration of 50 to 4,000 ppm. In some embodiments, the volume ratio of the plant extract and the geraniol may be 1:1 to 2:1 based on the same concentration, and some embodiments may include other ratios. This formulation may be mixed with other active ingredients or water to create a mixture or emulsion.

Some embodiments provide a method of controlling a plant-parasitic nematode, including managing a nematode by treating the nematode with the above composition. Some embodiments provide a method of creating an emulsion of the above formulation for use as a nematicide. Some embodiments contain a method of extraction of *Quillaja saponaria Molina* (Soapbark) oil or extract using alcohol extraction, hexane extraction, hot-water extraction, hypersonic distillation, $CO_2$ distillation, cold-water extraction, cold compression (expression), and steam distillation. Other extraction methods may also be used to acquire the active ingredient.

Some embodiments may include the use of *Quillaja saponaria Molina* as a filler, an extender, a wetting agent, a disintegrant, or a surfactant in the formulation. Some embodiments may include the use of *Quillaja brasiliensis* of other *Quillaja* plant species as active ingredients in the above formulation.

In some embodiments, the formulation may also comprise additional essential oils or active ingredients such as oxymatrine, castor oil, linseed oil, cedar oil, malic acid, cinnamon and cinnamon oil, mint and mint oil, citric acid, peppermint, peppermint oil, citronella, citronella oil, 2-Phenethyl propionate (2-phenylethyl propionate), cloves, clove oil, potassium sorbate, corn gluten meal, putrescent whole egg solids, corn oil, rosemary, rosemary oil, cottonseed oil, sesame (includes ground sesame plant) and sesame oil, dried blood, sodium chloride (common salt), eugenol, sodium lauryl sulfate, garlic and garlic oil, soybean oil, geraniol, thyme and thyme oil, geranium oil, white pepper, sodium lauryl sulfate, zinc, zinc metal, and lemongrass oil, etc. as well as all chemicals that make u these active ingredients. For example, cinnamaldehyde may be used as an active ingredient in place of cinnamon oil.

Here, the crops to be treated may include all known crops, and the formula may be delivered directly, delivered to the roots, the soil, leaves, or other areas of the plant where nematodes may be present. This provides methods of reduction to the loss of billions in agricultural revenue and production losses annually.

The present invention includes a formulation for controlling plant-parasitic nematodes that contains geraniol at a concentration of 500 to 4,000 ppm. The formula is derived from natural substances and is found to be environmentally friendly per the EPA under FIFRA 25(b), and in turn, exhibits a highly effective nematocidal control mechanism without causing plant phytotoxicity.

In the development of the present invention, nematocidal activity on root-knot nematodes (*Meloidogyne* spp.) was assessed using geraniol, azadirachtin, clove oil, oregano oil, pyrethrin, oxymatrine, neem extract, *Ostericum koreanum* extract, clove extract, *Myristica fragrans* extract, *Acorus gramineus* extract, *Kaempferia galanga* extract, *Quillaja saponaria Molina* and *Amomum cardamomum* L. extract. Based on the results, superior nematocidal activity was confirmed when geraniol was utilized alone or in combination with a oxymatrine, neem extract, clove extract, *Quillaja saponaria Molinaor Ostericum koreanum* extract. In particular, when geraniol was used at 500 to 4,000 ppm, superior nematocidal control was demonstrated without plant phytotoxicity. Still, plant phytotoxicity was shown to occur upon treatment with geraniol at 4,500 ppm or more. Other embodiments may include the use of other monoterpene alcohols in place of geraniol. In some embodiments, a plant extract selected from the group consisting of a oxymatrine, neem extract, an *Ostericum koreanum* extract, *Quillaja saponaria Molina* and a clove extract may be added. Here, the volume ratio of the plant extract and the geraniol is preferably 1:1 to 2:1 based on the same concentration.

The plant extracts may be acquired using a process selected from the group consisting of typically known extraction processes, such as alcohol extraction, hexane extraction, hot-water extraction, hypersonic distillation, CO2 distillation, cold-water extraction, cold compression (expression), and steam distillation.

V. CONTROLLING MOSQUITOS

Some embodiments are related to a composition for controlling mosquito and midge larvae and pupae containing plant essential oil, and more particularly to a composition for controlling mosquitoes comprising Garlic, Oxymatrine, Castor oil, Lemongrass, Geraniol, Cedarwood Oil.

Some embodiments aim to deliver a safer more naturally derived formulation for controlling Mosquitos and Midge adults, which provides superior adult activity without causing phytotoxicity and water or soil pollution due to residual toxicity. This formulation may be for controlling mosquitos and midges.

Some embodiments are configured to provide a safe and naturally derived material having larvicidal activity.

In the development of disclosed embodiments, seven types of plant-derived biological materials and twelve kinds of plant extracts were assessed for mosquitos and midge adult activity.

In the development of disclosed embodiments, mosquitos and midge adult activity on (*Ae. aegypti*), *Culex* species mosquitoes (*Cx. pipiens, Cx. tarsalis, Cx. quinquefasciatus*), *Anopheles* species mosquitoes (*An. freeborni* and *An. quadrimaculatus*) was assessed using Garlic, Oxymatrine, Castor oil, Lemongrass, Geraniol, Cedarwood Oil. Based on the results, superior mosquito and midge activity was confirmed when a formulation containing Garlic. Oxymatrine, Castor oil, Lemongrass, Geraniol, Cedarwood Oil was utilized in various combination with a Castor oil, Lemongrass, Geraniol, Cedarwood Oil oxymatrine, neem extract, clove extract, or *Ostericum koreanum* extract. In particular, when Gernaniol oil was used at 500 to 8,000 ppm, superior mosquito and midge control was demonstrated without plant phytotoxicity or water toxicology.

Therefore, some embodiments pertain to a formulation for controlling mosquitos and midge larvae or pupae containing geraniol oil at a concentration of 50 to 8,000 ppm.

The geraniol oil is monoterpene alcohol contained in plant essential oil and can be utilized without constraint as to the source plant. Geraniol also has low mammalian toxicity and is biodegradable, which makes it an advantageous ingredient to include in such composition.

It has been observed during the development of the embodiments that the mosquitos and midge adult activity may become insignificant if the quantity of geraniol oil in the composition for controlling mosquitos and midge adulticide activity is less than 5 ppm.

In some embodiments, the formulation for controlling mosquitos and midge adult activity may exhibit superior mosquito and midge adult activity even when containing geraniol oil alone. To demonstrate a higher and more stable mosquito and midge adult efficiency, a plant extract selected from the group consisting of an oxymatrine, neem extract, an *Ostericum koreanum* extract, Castor oil, Lemongrass, Geraniol, Cedarwood Oil, and a clove extract may be added. Here, the volume ratio of the plant extract and the geraniol oil is preferably 3:1 to 8:1 based on the same concentration.

The plant extracts may be acquired using a process selected from the group consisting of typically known extraction processes, such as alcohol extraction, hexane extraction, hot-water extraction, hypersonic distillation, CO2 distillation, cold-water extraction, cold compression (expression), and steam distillation.

In the present invention, the mosquitos and midge adult activity c (*Ae. aegypti*), *Culex* species mosquitoes (*Cx. pipiens, Cx. tarsalis, Cx. quinquefasciatus*), *Anopheles* species mosquitoes (*An. freeborni* and *An. quadrimaculatus*).

In some embodiments, the composition for controlling mosquito and midge adults may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some embodiments pertain to a formulation for controlling mosquito and midge adult, including the formulation for controlling mosquito and midge adult as an active ingredient, and to a method of controlling mosquito and midge adult including controlling mosquito and midge adult using the composition for controlling mosquito and midge adult.

Here, the areas to be treated are limitless and may include all known waterways, ponds, wet areas, and trees.

VI. CONTROLLING BACTERIA

In some embodiments, the RRA portal can either take the form of a website (to be opened in a computer browser), a mobile/tablet browser, or a specific application featured either for computers, phones, or tablets, which will be accessible for people who have bought or are employees of a company who has purchased these services.

Some embodiments are related to a composition for controlling Bacteria comprising plant essential oil, and more particularly to a composition for controlling insects comprising clove, rosemary, peppermint, tea tree oilseed, thyme, garlic, and cinnamon oil.

Some embodiments are related to a safer more naturally derived formulation for controlling Bacteria, which provides superior Bacteria activity without causing phytotoxicity and soil pollution due to residual toxicity, a formulation for controlling Bacteria including the same, and a method of controlling Bacteria.

Seven types of plant-derived biological materials and twelve plant extracts were assessed for fungicidal activity in the development of disclosed embodiments.

In the development of disclosed embodiments, insect activity on scab, blight, canker, leaf spot, mildew, blotch, wilt, and *botrytis* was assessed with a composition comprising Rosemary, sesame, peppermint, thyme, tea tree oilseed, cinnamon, palm oil, *Myristica fragrans* extract, *Acorus gramineus* extract, *Kaempferia galanga* extract, and *Amomum cardamomum* L. extract. Based on the results, superior fungicidal activity was confirmed when clove, rosemary, peppermint, tea tree oilseed, thyme, garlic, and cinnamon oil was used at 500 to 4,000 ppm, superior fungicidal control was demonstrated without plant phytotoxicity.

Therefore, some embodiments pertain to a formulation for controlling Bacteria containing clove, rosemary, peppermint, tea tree oilseed, thyme, garlic, and cinnamon oil l at a concentration of 50 to 4,000 ppm.

The clove, rosemary, peppermint, tea tree oilseed, thyme, garlic, and cinnamon oil, are monoterpene alcohol contained in plant essential oil and can be utilized without constraint as to the source plant.

In some embodiments, the fungicidal activity may become insignificant if the quantity of clove, rosemary, peppermint, tea tree oilseed, thyme, garlic, and cinnamon oil in the composition for controlling Bacteria is less than 50 ppm.

In some embodiments, the formulation for controlling Bacteria may exhibit superior fungicidal activity when containing clove, rosemary, peppermint, tea tree oilseed, thyme, garlic, and cinnamon oil. To demonstrate a higher and more stable fungicidal efficiency, a plant extract selected from the group consisting of a geranial, oxymatrine, neem extract, an *Ostericum koreanum* extract, and a clove extract may be added. Here, the volume ratio of the plant extract clove, rosemary, peppermint, tea tree oilseed, thyme, garlic, and cinnamon oil is preferably 3:1 to 6:1 based on the same concentration. If the volume ratio of the plant extract and clove, rosemary, peppermint, tea tree oilseed, thyme, garlic, and cinnamon oil falls out of the above range, there is a concern that phytotoxicity may occur.

The plant extracts may be acquired using a process selected from the group consisting of typically known extraction processes, such as alcohol extraction, hexane extraction, hot-water extraction, hypersonic distillation, $CO2$ distillation, cold-water extraction, cold compression (expression), and steam distillation.

In some embodiments, the insects may be demonstrated as scab, blight, canker, leaf spot, mildew, blotch, wilt, or *botrytis*.

In some embodiments, the composition for controlling Bacteria may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Another aspect of the present invention pertains to a formulation for Bacteria including the formulation for controlling Bacteria as an active ingredient, and to a method of controlling Bacteria including controlling Bacteria using the composition for controlling Bacteria.

Here, the crops to be treated may include all known crops, and the formula may be delivered directly, delivered to the roots, the soil, leaves, or other areas of the plant. This provides methods of reduction to the loss of billions in agricultural revenue and production losses annually.

VII. CONTROLLING INSECTS

In some embodiments, the color coding between green to yellow to red may be based on absolute values, such as certain colors dependent on if they fall under certain ranges of compliance, and in other embodiments, the coloring may be based on relative values, such as being a red color if the company falls under a certain percentile of governance relative to its industry rivals as compared to a green color if the same company is over a certain percentile of governance compliance.

Some embodiments are related to a composition for controlling insects containing plant essential oil, and more particularly to a composition for controlling insects containing Rosemary, sesame, peppermint, thyme, tea tree oilseed, cinnamon, and palm oil.

Some embodiments are configured to provide a safe and naturally derived material having insecticidal activity.

In the development of disclosed embodiments, seven types of plant-derived biological materials and twelve kinds of plant extracts were assessed for insecticidal activity.

In the development of disclosed embodiments, insect activity on mites, *thrips*, aphids, whitefly, mealybug, gnats, slugs, midges, leafhoppers, skeletonizes, psyllids, flies, and ants was assessed Rosemary, sesame, peppermint, thyme, tea tree oilseed, cinnamon, palm oil, *Myristica fragrans* extract, *Acorus gramineus* extract, *Kaempferia galanga* extract, and *Amomum cardamomum* L. extract. Based on the results, superior insecticidal activity was confirmed when rosemary, sesame, peppermint, thyme, tea tree oilseed, cinnamon, and palm oil were utilized together. In particular, when Rosemary, sesame, peppermint, thyme, tea tree oilseed, cinnamon, and palm oil was used at 500 to 4,000 ppm, superior insecticidal control was demonstrated without plant phytotoxicity.

Therefore, some embodiments pertain to a formulation for controlling insects containing Rosemary, sesame, peppermint, thyme, tea tree oilseed, cinnamon, and palm oil at a concentration of 50 to 4,000 ppm.

Rosemary, sesame, peppermint, thyme, tea tree oilseed, cinnamon, and palm oil are monoterpene alcohol contained in plant essential oil and can be utilized without constraint as to the source plant.

In some embodiments, the insecticidal activity may become insignificant if the quantity of Rosemary, sesame, peppermint, thyme, tea tree oilseed, cinnamon, and palm oil in the composition for controlling insects is less than 50 ppm.

In some embodiments, the formulation for controlling insects may exhibit superior insecticidal activity when containing Rosemary, sesame, peppermint, thyme, tea tree oilseed, cinnamon, and palm oil. To demonstrate a higher and more stable insecticidal efficiency, a plant extract selected from the group consisting of a geranial, oxymatrine, neem extract, an *Ostericum koreanum* extract, and a clove extract may be added. Here, the volume ratio of the plant extract Rosemary, sesame, peppermint, thyme, tea tree oilseed, cinnamon, and palm oil is preferably 3:1 to 6:1 based on the same concentration. If the volume ratio of the plant extract and the Rosemary, sesame, peppermint, thyme, tea tree oilseed, cinnamon, and palm oil falls out of the above range, there is a concern that phytotoxicity may occur.

The plant extracts may be acquired using a process selected from the group consisting of typically known extraction processes, such as alcohol extraction, hexane extraction, hot-water extraction, hypersonic distillation, $CO_2$ distillation, cold-water extraction, cold compression (expression), and steam distillation.

In some embodiments, the insects may be demonstrated as mites, *thrips*, aphids, whitefly, mealybug, gnats, slugs, midges, leafhoppers, skeletonizes, psyllids, flies, or any other insects that are not disclosed herein.

In some embodiments, the composition for controlling insects may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some embodiments pertain to a formulation for insects including the formulation for controlling insects as an active ingredient, and to a method of controlling insects including controlling insects using the composition for controlling insects.

Here, the crops to be treated may include all known crops, and the formula may be delivered directly, delivered to the roots, the soil, leaves, or other areas of the plant. This provides methods of reduction to the loss of billions in agricultural revenue and production losses annually.

VIII. CONTROLLING FUNGUS

Some embodiments may include a graph comparing the Risk Quotient compared with other companies in terms of a range of market cap, geography, company size, subindustry, or other means of separating individual companies into groups that can be further analyzed for governance compliance.

Some embodiments are related to a composition for controlling fungus containing plant essential oil, and more particularly to a composition for controlling insects containing Rosemary, sesame, peppermint, thyme, tea tree oilseed, cinnamon, and palm oil.

Some embodiments are configured to provide a safe and naturally derived material having fungicidal activity.

In the development of some embodiments, seven types of plant-derived biological materials and twelve kinds of plant extracts were assessed for fungicidal activity.

In the development of some embodiments, fungi activity on blights, rots, mildews, *Phomopsis*, molds, and anthracnose was assessed Rosemary, sesame, peppermint, thyme, tea tree oilseed, cinnamon, palm oil, *Myristica fragrans* extract, *Acorus gramineus* extract, *Kaempferia galanga* extract, and *Amomum cardamomum* L. extract. Based on the results, superior fungicidal activity was confirmed when clove, rosemary, peppermint, tea tree oilseed, white mineral oil, citrus pulp, and palm oil were utilized together. In particular, when clove, rosemary, peppermint, tea tree oilseed, white mineral oil, citrus pulp, and palm oil were used at 500 to 4,000 ppm, superior fungicidal control was demonstrated without plant phytotoxicity.

Therefore, some embodiments pertain to a formulation for controlling fungus containing clove, rosemary, peppermint, tea tree oilseed, white mineral oil, citrus pulp, and palm oil at a concentration of 50 to 4,000 ppm.

The clove, rosemary, peppermint, and tea tree oilseed may have monoterpene alcohol contained in the plant essential oil and can be utilized without constraint as to the source plant.

In some embodiments, the fungicidal activity may become insignificant if the quantity of clove, rosemary, peppermint, tea tree oilseed, white mineral oil, citrus pulp, and palm oil in the composition for controlling fungus is less than 50 ppm.

In some embodiments, the formulation for controlling fungus may exhibit superior fungicidal activity when containing clove, rosemary, peppermint, tea tree oilseed, white mineral oil, citrus pulp, and palm oil. To demonstrate a higher and more stable fungicidal efficiency, a plant extract selected from the group consisting of a geranial, oxymatrine, neem extract, an *Ostericum koreanum* extract, and a clove extract may be added. Here, the volume ratio of the plant extract clove, rosemary, peppermint, tea tree oilseed, white mineral oil, citrus pulp, and palm oil is preferably 3:1 to 6:1 based on the same concentration. If the volume ratio of the plant extract and the clove, rosemary, peppermint, tea tree oilseed, white mineral oil, citrus pulp, and palm oil falls out of the above range, there is a concern that phytotoxicity may occur.

The plant extracts may be acquired using a process selected from the group consisting of typically known extraction processes, such as alcohol extraction, hexane extraction, hot-water extraction, hypersonic distillation, CO2 distillation, cold-water extraction, cold compression (expression), and steam distillation.

In some embodiments, the insects may be demonstrated as blights, rots, mildews, *Phomopsis*, molds, or anthracnose.

In In some embodiments, the composition for controlling fungus may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some other embodiments pertain to a formulation for fungus including the formulation for controlling fungus as an active ingredient, and to a method of controlling fungus including controlling fungus using the composition for controlling fungus.

Here, the crops to be treated may include all known crops, and the formula may be delivered directly, delivered to the roots, the soil, leaves, or other areas of the plant. This provides methods of reduction to the loss of billions in agricultural revenue and production losses annually. Here, the crops to be treated for fungus issues can be soybeans, wheat, tomatoes, strawberries, cane berries, corn, grapes, onions, peppers, citrus, cucurbits, apples, pears, potatoes, and beans. These fungus issues cause billions in crop losses annually.

IX. CONTROLLING NEMATODES AND FUNGUS

Some embodiments are related to a composition for controlling nematodes and fungus containing plant essential oil, and more particularly to a composition for controlling plant-parasitic nematodes and fungus containing spearmint, garlic oil, clove oil, and thyme oil.

The present invention is designed to provide a safe and naturally derived material having nematocidal and fungicidal activity.

In the development of disclosed embodiments, seven types of plant-derived biological materials and twelve kinds of plant extracts were assessed for nematocidal and fungicidal activity.

In the development of disclosed embodiments, nematocidal and fungicidal activity on root-knot nematodes (*Meloidogyne* spp.) and blights, mildew, wilts, and cankers were assessed spearmint, garlic oil, clove oil, thyme oil, *Myristica fragrans* extract, *Acorus gramineus* extract, *Kaempferia galanga* extract, and *Amomum cardamomum* L. extract. Based on the results, superior nematocidal and fungicidal activity was confirmed when spearmint, garlic oil, clove oil, and thyme oil was utilized together. In particular, when spearmint, garlic oil, clove oil, and thyme oil was used at 500 to 4,000 ppm, superior nematocidal and fungicidal control was demonstrated without plant phytotoxicity.

Therefore, some embodiments pertain to a formulation for controlling plant-parasitic nematodes containing spearmint, garlic oil, clove oil, thyme oil at a concentration of 50 to 4,000 ppm.

Spearmint, garlic oil, clove oil, and thyme oil are monoterpene alcohol contained in plant essential oil and can be utilized without constraint as to the source plant.

In some embodiments, the nematocidal and fungicidal activity may become insignificant if the quantity of geraniol in the composition for controlling plant-parasitic nematodes is less than 50 ppm.

In some embodiments, the formulation for controlling plant-parasitic nematodes and fungus diseases may exhibit superior nematocidal and fungicidal activity when containing spearmint, garlic oil, clove oil, and thyme oil. To demonstrate a higher and more stable nematocidal efficiency, a plant extract selected from the group consisting of a geranial, oxymatrine, neem extract, an *Ostericum koreanum* extract, and a clove extract may be added. Here, the volume ratio of the plant extract and the geraniol is preferably 3:1 to 6:1 based on the same concentration. If the volume ratio of the plant extract and the spearmint, garlic oil, clove oil, and thyme oil falls out of the above range, there is a concern that phytotoxicity may occur.

The plant extracts may be acquired using a process selected from the group consisting of typically known extraction processes, such as alcohol extraction, hexane extraction, hot-water extraction, hypersonic distillation, CO2 distillation, cold-water extraction, cold compression (expression), and steam distillation.

In some embodiments, the plant-parasitic nematodes may be demonstrated by root-knot nematodes, root-lesion nematodes, spiral nematodes, cyst nematodes, and multiple other plant-parasitic nematodes.

Root-knot nematodes infest thousands of different plant species including vegetables, fruits, and row crops. Cyst nematodes are known to infest tobacco, cereals, sugar beets, potato, rice, corn, soybeans, and many other crops. *Heterodera schachtii* (BCN) principally attacks sugar beets, and *Heterodera avenae* is a pest of cereals. *Heterodera zeae* feeds on corn, and *Globodera rostochiensis* and *G. pallida* feed on potatoes. The soybean cyst nematode (SCN) is present in every soybean-producing state in the US, and causes total soybean yield losses estimated to be nearly $1 billion per year. Once SCN is present in a field, it cannot feasibly be eradicated using known methods. Although soybean is the major economic crop attacked by SCN, SCN attacks some fifty hosts in total, including field crops, vegetables, ornamentals, and weeds.

Tea tree oil root-knot nematode (RKN) is a destructive nematode, which forms galls on the roots of tea tree oil plants. The causative agent is *Meloidogyne incognita* (Kofoid and White) Chitwood, a nematode that can infest a variety of plant species. Nutrient and water uptake are decreased in infested plants, and plants may become susceptible to pathogens, especially *Fusarium* wilt. Consequently, yield is decreased in plants infested with RKN. In the US alone, an estimated 10.93% of tea tree oil yield loss in 2004 was attributed to RKN which is widespread throughout the U.S. Tea tree oil Belt. Methods to mitigate RKN damage include rotating tea tree oil crops with non-susceptible crops and the application of costly nematicides. However, the most effective way for tea tree oil growers to reduce yield loss and crop damage due to RKN is to grow RKN resistant tea tree oil cultivars.

In some embodiments, the composition for controlling plant-parasitic nematodes and fungus may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some other embodiments pertain to a formulation for controlling plant-parasitic nematodes, and fungus, including the formulation for controlling plant-parasitic nematodes and fungus as an active ingredient, and to a method of controlling plant-parasitic nematodes and fungus including controlling nematodes and fungus using the composition for controlling plant-parasitic nematodes and fungus.

Here, the crops to be treated may include all known crops, and the formula may be delivered directly, delivered to the roots, the soil, leaves, or other areas of the plant. This provides methods of reduction to the loss of billions in agricultural revenue and production losses annually. Here, the crops to be treated for fungus issues can be soybeans, wheat, tomatoes, strawberries, cane berries, corn, grapes, onions, peppers, citrus, cucurbits, apples, pears, potatoes, beans, and all other known crops and plants. These fungus issues cause billions in crop losses annually. Use cases may be for commercial use, home use, or any use to reduce pests that may be in a given area that cause harm to plants.

X. CONTROLLING LARVAE AND INSECTS WITH OXYMATRINE

Some embodiments are related to a composition for controlling insects containing plant essential oil, and more particularly to a composition for controlling insects containing oxymatrine oil.

Some embodiments are related to a formulation for controlling insects that contains oxymatrine at a concentration of 500 to 6,000 ppm is derived from natural substances and is found to be environmentally friendly per the EPA under FIFRA 25 (b), and in turn exhibits highly effective insecticidal control mechanism without causing plant phytotoxicity.

The present invention is configured to provide a safe and naturally derived material having insecticidal activity.

In the development of disclosed embodiments, seven types of plant-derived biological materials and twelve kinds of plant extracts were assessed for insecticidal activity.

In the development of disclosed embodiments, insecticidal activity on multiple insects was assessed oxymatrine extract, Acorus gramineous extract, *Kaempferia galanga* extract, and *Amomum cardamomum* L. extract. Based on the results, superior insecticidal activity was confirmed when oxymatrine was utilized. In particular, when Oxymatrine was used at 500 to 6,000 ppm, superior insecticidal control was demonstrated without plant phytotoxicity.

Therefore, some embodiments pertain to a formulation for controlling insects containing Oxymatrine at a concentration of 50 to 6,000 ppm.

The Oxymatrine, may be a monoterpene alcohol contained in plant essential oil and can be utilized without constraint as to the source plant.

In some embodiments, the insecticidal activity may become insignificant if the quantity of Oxymatrine in the composition for controlling insects is less than 50 ppm.

According to some embodiments, the formulation for controlling insects may exhibit superior insecticidal activity when containing oxymatrine oil. To demonstrate a higher and more stable insecticidal efficiency, a plant extract selected from the group consisting of a geranial, oxymatrine, neem extract, an *Ostericum koreanum* extract, and a clove extract may be added. Here, the volume ratio of the plant extract oxymatrine oil is preferably 3:1 to 6:1 based on the same concentration. If the volume ratio of the plant extract and the oxymatrine oil falls out of the above range, there is a concern that phytotoxicity may occur.

The plant extracts may be acquired using a process selected from the group consisting of typically known extraction processes, such as alcohol extraction, hexane extraction, hot-water extraction, hypersonic distillation, $CO_2$ distillation, cold-water extraction, cold compression (expression), and steam distillation.

In some embodiments, the composition for controlling insects may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some other embodiments pertain to a formulation for insecticidal including the formulation for controlling insects as an active ingredient, and to a method of controlling insects including controlling insects using the composition for controlling insects.

Here, the crops to be treated may include all known crops, and the formula may be delivered directly, delivered to the roots, the soil, leaves, or other areas of the plant. This provides methods of reduction to the loss of billions in agricultural revenue and production losses annually.

XI. CONTROLLING INSECTS WITH TEA SAPONIN

Some embodiments are related to a composition for controlling insects containing plant essential oil, and more particularly to a composition for controlling insects containing tea saponin.

Tea Saponin may be used against fungi and bacteria and will be used for sigatoka and snails. Tea saponin may be used to reduce or eliminate other pests, but has been found to greatly reduce or entirely eliminate black sigatoka fungus and snails.

Some embodiments aim to deliver a safer more naturally derived formulation for controlling insects, which provides superior insect activity without causing phytotoxicity and soil pollution due to residual toxicity, a formulation for controlling insects including the same, and a method of controlling slugs and snails and pests alike.

Some embodiments are configured to provide a safe and naturally derived material having insecticidal activity.

In the development of disclosed embodiments, seven types of plant-derived biological materials and twelve kinds of plant extracts were assessed for insecticidal activity.

In the development of disclosed embodiments, insecticidal activity on multiple insects was assessed tea saponin extract, *Acorus gramineous* extract, *Kaempferia galanga* extract, and *Amomum cardamomum* L. extract. Based on the results, superior insecticidal activity was confirmed when tea saponin was utilized. In particular, when tea saponin was used at 500 to 6,000 ppm, superior insecticidal control was demonstrated without plant phytotoxicity.

Therefore, an aspect of the current invention pertains to a formulation for controlling insects containing tea saponin at a concentration of 50 to 6,000 ppm.

The tea saponin, is monoterpene alcohol contained in plant essential oil and can be utilized without constraint as to the source plant.

In some embodiments, the insecticidal activity may become insignificant if the quantity of tea saponin in the composition for controlling insects is less than 50 ppm.

In some embodiments, the formulation for controlling insects may exhibit superior insecticidal activity when containing tea saponin oil. To demonstrate a higher and more stable insecticidal efficiency, a plant extract selected from the group consisting of a geranial, oxymatrine, neem extract, an *Ostericum koreanum* extract, and a clove extract may be added. Here, the volume ratio of the plant extract oxymatrine oil is preferably 3:1 to 6:1 based on the same concentration.

The plant extracts may be acquired using a process selected from the group consisting of typically known extraction processes, such as alcohol extraction, hexane extraction, hot-water extraction, hypersonic distillation, CO2 distillation, cold-water extraction, cold compression (expression), and steam distillation.

In some embodiments, the composition for controlling insects may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some other embodiments pertain to a formulation for insecticidal including the formulation for controlling insects as an active ingredient, and to a method of controlling insects including controlling insects using the composition for controlling insects.

Here, the crops to be treated may include all known crops, and the formula may be delivered directly, delivered to the roots, the soil, leaves, or other areas of the plant. This provides methods of reduction to the loss of billions in agricultural revenue and production losses annually.

XII. CONTROLLING VARIOUS INSECTS WITH GERANIOL

Some embodiments are related to a composition for controlling fungus containing plant essential oil, and more particularly to a composition for controlling insects containing Geraniol oil.

Some embodiments aim to deliver a safer more naturally derived formulation for controlling fungus, which provides superior fungus activity without causing phytotoxicity and soil pollution due to residual toxicity, a formulation for controlling fungus including the same, and a method of controlling fungus.

Some embodiments are configured to provide a safe and naturally derived material having fungicidal activity.

In the development of disclosed embodiments, seven types of plant-derived biological materials and twelve kinds of plant extracts were assessed for fungicidal activity.

In the development of disclosed embodiments, fungicide activity on mildew, and anthracnose was assessed Geraniol oil, *Myristica fragrans* extract, *Acorus gramineus* extract, *Kaempferia galanga* extract, and *Amomum cardamomum* L. extract. Based on the results, superior fungicidal activity was confirmed when Geraniol oil was utilized together. In particular, when Geraniol oil was used at 500 to 4,000 ppm, superior fungicidal control was demonstrated without plant phytotoxicity.

Therefore, some embodiments pertain to a formulation for controlling fungus containing Geraniol oil at a concentration of 50 to 4,000 ppm.

Geraniol is a monoterpene alcohol contained in plant essential oil and can be utilized without constraint as to the source plant.

In some embodiments, the repellent compositions and formulations thereof may contain geraniol oil. While some of the compositions are referred to as "geraniol-based" this designation is not intended to imply any specific quantity or proportion of geraniol. It is merely to convey that the compositions contain geraniol.

Geraniol, (3,7-dimethyl-2,6-octadien-1-ol; CAS Reg. No. 106-24-1; C10H180) is a clear to pale yellow monoterpenoid alcohol which exists as an oily liquid. It is insoluble in water but soluble in most common organic solvents. It has a rose-like odor, for which it is commonly used in perfumes. It is the primary part of oil-of-rose and palmarosa oil. It also occurs in small quantities in Geranium, Lemon, Citronella, and many other essential oils. Geraniol may be derived directly from geranium plants engineered to produce larger amounts of geraniol or from lemongrass or other herbs. It is typically extracted from geranium oil through a refining process.

While geraniol is used in insect repellants or deterrents to repel mosquitoes, house flies, stable flies, horn flies, cockroaches, fire ants, fleas, gnats, dog ticks, lone star ticks, no-see-ums, mite, crickets, earwigs, silverfish and lice, it is not known to have bird or non-insect repellant functionalities.

Surprisingly, it has been discovered that geraniol oil, in combination with castor oil, and mint does indeed have both bird and non-insect repellent properties as well as the killing of some organisms including scales.

In some embodiments, geraniol oil may be present in the compositions of the present invention from about 0.05% by weight to about 30% by weight, but may be higher in concentrated formulations. In one embodiment, geraniol is present in an amount from 3-25% by weight. In a further embodiment, it is present in an amount by weight of from 5-40%. In addition, geraniol oil may be present in amounts between or bounded by the concentrations disclosed herein. For example, the weight percentages 0.05-1%, 2-3%, 20-30%, 3-10%, 15-25%, 5-10%, and 15-20% are within the scope of the invention.

In some embodiments, the fungicidal activity may become insignificant if the quantity of Geraniol oil in the composition for controlling fungus is less than 50 ppm.

In some embodiments, the formulation for controlling fungus may exhibit superior fungicidal activity when containing Geraniol oil. To demonstrate a higher and more stable fungicidal efficiency, a plant extract selected from the group consisting of a geranial, oxymatrine, neem extract, an *Ostericum koreanum* extract, and a clove extract may be added. Here, the volume ratio of the plant extract geraniol oil is preferably 3:1 to 6:1 based on the same concentration. If the volume ratio of the plant extract and the Geraniol oil falls out of the above range, there is a concern that phytotoxicity may occur.

The plant extracts may be acquired using a process selected from the group consisting of typically known extraction processes, such as alcohol extraction, hexane extraction, hot-water extraction, hypersonic distillation, $CO_2$ distillation, cold-water extraction, cold compression (expression), and steam distillation.

In the present invention, the composition for controlling fungus may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some other embodiments pertain to a formulation for fungus including the formulation for controlling fungus as an active ingredient, and to a method of controlling fungus including controlling fungus using the composition for controlling fungus.

Here, the crops to be treated may include all known crops, and the formula may be delivered directly, delivered to the roots, the soil, leaves, or other areas of the plant. This provides methods of reduction to the loss of billions in agricultural revenue and production losses annually.

XIII. CONTROLLING BLACK SIGATOKA

Some embodiments are related to a composition for controlling black Sigatoka containing plant essential oil, and more particularly to a composition for controlling black Sigatoka containing tea tree extract.

Some embodiments are configured to provide a safe and naturally derived material having black Sigatoka activity.

Black Sigatoka, also known as black leaf streak, is the most economically important leaf spot disease of bananas in the region affecting a wide range of cultivars and often completely defoliating more vulnerable cultivars before fruit bunches are mature. It is caused by the airborne fungus *Mycosphaerella fijiensis* Morelet, which is spread from tree to tree by wind, rain, and irrigation water splashes.

The fungal pathogen infects plants and impedes photosynthesis by blackening parts of the leaves, eventually killing the entire leaf. Characteristic symptoms include dark leaf spots that eventually enlarge and coalesce, causing much of the leaf area to turn yellowish and brown. Often infected plants show early death of the leaves and develop large brownish-colored streaks on the underside especially of the fourth leaf. The streaks, which are numerous, coalesce later resulting in black necrotic patches appearing on the topside of the leaf. The blackened (necrotic) areas dry out rapidly and turn brown.

When soaked by rain they tend to become much darker and give the field an unsightly look of black dead leaves. The leaf blade edges, which are often the most affected parts, tend to fold on themselves. High rainfall and humidity favor disease development.

The scientific name of a fungus changes whether it is in its sexual (teleomorph) stage or its asexual stage (anamorph). *Mycosphaerella fijiensis* is the sexual stage of the pathogen of Black Sigatoka. The asexual form (anamorph) of this fungus is called *Pseudocercospora fijiensis* and produces conidia spores. The conidia germinate during periods of high relative humidity (92-100% RH) and infect the leaf through leaf openings such as the stoma.

This infection will form lesions on the undersurface of the leaf. As the lesion matures, conidia and hyphae cluster together to form spermatogonia (fungal structures that produce male reproductive cells, spermatia). Spermatia fertilize receptive neighboring female hyphae, and form pseudothecia that contain sexual spores (ascospores). For a more detailed description of the life cycle of this fungus, please see the illustration by Bennett and Arneson (2003). A similar life cycle can be seen for Yellow Sigatoka, in which the teleomorph is *M. musicola* and the anamorph is *P. musae*. Windborne ascospores are the major inoculum for Black Sigatoka, whereas the inoculum of Yellow Sigatoka consists of both conidia (water-dispersed) and ascospores. The first symptom (chlorotic flecking) appears about 15-20 days after infection. The fungus survives on dead banana leaves as spores or mycelium and will 53 mulsifiable healthy tissues.

Although both pathogens prefer high humidity, black Sigatoka is more common in warmer environments, whereas Yellow Sigatoka is more common in cooler environments. Black Sigatoka produced ascospores 2 weeks after the appearance of leaf streaks, but Yellow Sigatoka produced them about 4 weeks after the streaks appear. In general, Black Sigatoka is a more challenging pathogen to manage than Yellow Sigatoka.

The resulting intensive use of fungicides is a major concern for the environment and human health. This intensive use of fungicides is mainly because of the development of resistance to synthetic fungicides by the pathogen populations. The global search for plant-protection solutions, that are both environmentally safe and efficacious, is an important aspect of sustainable agriculture. This is driven by the need to supply food to the ever-growing world population, and the call for chemical load reduction.

Tea tree oil, an essential oil extracted from the plant *Melaleuca* alternifolia, contains many components, mostly terpenes, and their alcohols, and has been shown to be an effective antiseptic, fungicide, and bactericide and more recently against fungal plant pathogens. Until the last decade, this essential oil had not been tested against plant pathogens in field-grown agricultural crops.

Based on tea tree oil, as an active ingredient, a natural fungicide Timorex Gold (22.3 EC W/V), was prepared for use on plant tissue. This product was found to be effective against a broad range of plant-pathogenic fungi in numerous crops, including vegetables, herbs, grapevines, bananas, and fruit trees. Recently, the activity of tea tree oil against *Mycosphaerella fijiensis* and its efficacy against black Sigatoka in field-grown banana plants in South and Central America was tested. The study may suggest that it represents an additional alternative to existing treatments for controlling black Sigatoka in banana plantations.

Tea tree oil was used in disclosed experiments and trials as an 54 mulsifiable concentrated formulation. For field trials in bananas, tea tree oil was applied similarly to conventional synthetic fungicides, with mineral oil, surfactants, and/or just water. The following fungicides, registered for use against black sigatoka in bananas, were tested for comparison: azoxystrobin (Bankit 25 SC), trifloxystrobin (Flint, Tega 50 WG), difenoconazole (Score, Sico 25 EC), mancozeb (43 SC Duwest 80 WP), flutriafol (Impact, 125 SC) and tridemorph (Calixin 86 OL).

The sensitivity of *Mycosphaerella fijiensis* ascospores to Timorex Gold was examined. Dry leaf tissue from a banana leaf on stage 6 black Sigatoka lesions containing mature pseudothecia was collected at Monreri Experimental Farm, located on the Atlantic Coast of Costa Rica. The selected tissue was incubated for 48 h at 26° C. in plastic bags with a moist paper towel. The infected samples were then removed from the plastic bag and cut into small pieces of 1-2 cm. The paper with the attached leaf pieces was submerged for 5 minutes in distilled water and then immediately placed inside the top of a petri dish for thirty minutes to allow ascospores to discharge over the dish containing 2% water agar amended with various concentrations of tea tree oil. The paper and leaf tissue were then removed and the dishes were incubated at 26° C. for 48 hours to allow the ascospores to germinate. The percentage of germinated ascospores was recorded and the inhibition was calculated for each concentration, as a percentage of the germination rate in the controls.

Some studies reveal that tea tree oil effectively inhibited the germination of ascospores of *M. fijiensis*: at concentrations of 10, 100, and 1000 ppm it inhibited germination of *M. fijiensis* ascospores on 2% water agar by 21, 39 and 100%, respectively, relative to the control. In experiments conducted, all evaluated tissue samples either coming from the commercial farms or from the wild plants, showed a similar percentage inhibition of the elongation of the germ tube. In most cases, the inhibition was dependent on the tea tree oil concentration. As product concentration increased, the inhibition percentage of the elongation of the germinating tube also increased. At 10 ppm concentration inhibition ranged between 43 and 78%. As concentration increased results became more homogeneous, and at 100 ppm concentration inhibition range was between 73 and 85%. At 1000 ppm inhibition was 100% in all samples.

The fungicidal and antimicrobial activities of tea tree oil against fungal pathogens arise from its ability to disrupt the permeability barrier of living organisms' membrane structures. In yeast cells and isolated mitochondria, extract of tea tree components destroys cellular integrity, inhibits respiration and ion transport processes, and increases membrane permeability. Results obtained with transmission electron microscopy showed that tea tree oil disrupted the fungal cell wall and cell membrane of *M. fijiensis* at stages 4 or 5 of fungal development in the intracellular space of banana leaf mesophyll. This may account for the strong curative activity of tea tree oil against black Sigatoka. A similar effect was observed by Shao et al. against *Botrytis cinerea*. As each compound has a different mode of action, these modifications could be incorporated into a disease-management program that would minimize the risk of resistance development by *M. fijiensis* and, at the same time, maximize disease control.

The present study showed that either trifloxystrobin or difenoconazole effectively controlled Black Sigatoka when applied as tank mixes with tea tree oil. Fungicides are combined in mixtures mainly: to widen the spectrum of antifungal activity and to extend its duration; to exploit the synergistic interaction between the compounds, whereby the overall activity can be increased or the amounts used can be reduced without loss of activity; and to delay or reduce the emergence of resistant strains. The similarity of the efficacies of the tank mixes of systemic fungicides and tea tree oil suggests that the tank-mix treatment can be considered as a strategy for the control of Black Sigatoka. Although in principle, combinations of synthetic antifungal compounds could be used to reduce the chemical load of any particular compound applied to crops, concerns about resistance development at lower doses have militated against their use as advised by the Fungicide Resistance Action Committee (FRAC).

Essential tea tree oil, a multicomponent compound, exhibits multisite functional activity and a very low probability of promoting resistance or cross-resistance in plant pathogens. Therefore, may be an important tool for inclusion in spray programs, to avoid cross-resistance development during the season. It can be rotated in applications with products to which *M. fijiensis* populations have shown a loss of sensitivity. Therefore, tea tree oil products (Timorex Gold) may constitute an attractive alternative for controlling black Sigatoka and various other diseases in banana plantations and can be used in both organic and conventional systems.

Depending on factors such as cultivar, location, cultural practices, and fungicide(s) selected, up to 24 fungicide spray applications per year may be needed to produce acceptable banana yields at large plantations in places like Hawaii. Below disclosed embodiments are related to naturally derived compositions that are configured to fight black Sigatoka disease for crops like bananas and plantains.

In the development of disclosed embodiments, seven types of plant-derived biological materials and twelve kinds of plant extracts were assessed for black Sigatoka activity.

In the development of disclosed embodiments, black Sigatoka was assessed using tea, tree, geraniol, azadirachtin, clove oil, oregano oil, pyrethrin, oxymatrine, neem extract, *Ostericum koreanum* extract, clove extract, *Myristica fragrans, Myrtaceae, Poaceae*, and *Lauraceae* extract, *Acorus gramineus* extract, *Kaempferia galanga* extract, and *Amomum cardamomum* L. extract. Based on the results, superior black Sigatoka activity was confirmed when tea tree was utilized alone or in combination with a Myrtaceae, Poaceae, and Lauraceae extract. In particular, when Tea Tree was used at 500 to 4,000 ppm, superior black Sigatoka control was demonstrated without plant phytotoxicity.

Therefore, some embodiments pertain to a formulation for controlling black Sigatoka containing tea tree at a concentration of 50 to 4,000 ppm.

The tea tree is monoterpene alcohol contained in plant essential oil and can be utilized without constraint as to the source plant.

In some embodiments, the monoterpene activity may become insignificant if the quantity of tea tree in the composition for controlling black Sigatoka is less than 50 ppm. On the other hand, if the amount exceeds 4,500 ppm, phytotoxicity may be caused in crops.

In some embodiments, the formulation for controlling black Sigatoka may exhibit superior fungicidal activity even when containing tea tree alone. To demonstrate a higher and more stable fungicidal efficiency, a plant extract selected from the group consisting of geraniol, oxymatrine, neem extract, an *Ostericum koreanum*, Myrtaceae, Poaceae, and Lauraceae extract, and a clove extract may be added. Here, the volume ratio of the plant extract and the geraniol is preferably 3:1 to 6:1 based on the same concentration.

The plant extracts may be acquired using a process selected from the group consisting of typically known extraction processes, such as alcohol extraction, hexane extraction, hot-water extraction, hypersonic distillation, CO2 distillation, cold-water extraction, cold compression (expression), and steam distillation.

In the development disclosed embodiments, black sigatoka was also assessed using tea, tree, geraniol, azadirachtin, clove oil, oregano oil, pyrethrin, oxymatrine, neem extract, *Ostericum koreanum* extract, clove extract, *Myristica fragrans, Myrtaceae, Poaceae*, and *Lauraceae* extract, *Acorus gramineus* extract, *Kaempferia galanga* extract, and *Amomum cardamomum* L. extract. Based on the results, superior black sigatoka activity was confirmed when tea tree was utilized alone or in combination with a Myrtaceae, Poaceae, and Lauraceae extract. In particular, when Tea Tree was used at 500 to 4,000 ppm, superior black sigatoka control was demonstrated without plant phytotoxicity.

The black sigatoka fungus is a plant pathogen that causes black leaf streak disease in bananas. The disease is characterized by black streaks on the leaves of the plant, which can eventually lead to death. Tea tree oil extract has been shown to be effective in controlling the black sigatoka fungus. Geraniol oil is also effective against the fungus, but at higher concentrations, it can cause phytotoxicity and soil pollution. The proposed fungicide would include the tree oil extract at a ratio of 4:1, in addition to geraniol oil at a concentration of 50-4000 ppm. This formulation would be safer and more naturally derived, and would not cause phytotoxicity or soil pollution.

Other embodiments may allow formulations of up to 30% tea tree oil/extract. This may allow the formulation to perform better than mancozeb (or other dithiocarbamate non-systemic agricultural fungicides). Certain embodiments may include the use of dithiocarbamate non-systemic fungicides in addition to or within the formulation of the fungicide containing tea tree oil.

Therefore, an aspect of the current invention pertains to a formulation for controlling black sigatoka containing tea tree at a concentration of 50 to 4,000 ppm.

In some embodiments, the composition for controlling black Sigatoka may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, liquid paraffin, and normal saline. More preferably, secondary distilled water added with 0.1 ml of Triton X-100 per liter (L) is used.

Some other embodiments pertain to a formulation for controlling black Sigatoka, including the formulation for controlling black Sigatoka as an active ingredient, and to a method of controlling black Sigatoka including controlling black Sigatoka using the composition for controlling black Sigatoka.

XIV. INCREASING FLOWER HOLD AND BEE ATTRACTION

Some embodiments are related to a composition for increasing a plant's ability to increase growth, increase stamen development and hold, maintain metabolism during abiotic and biotic stress and increase attraction to the flower by bees while using a blend consisting of fertilizers, propolis, cytokinin, gibberellins, auxins, abscisic acid, brassinosteroids, fucoxanthin, jasmonic and salicylic acid and kelp.

Some embodiments aim to deliver a safer more naturally derived formulation for increasing plants bloom and yields, which provides superior plant support activity without causing phytotoxicity, or soil pollution due to residual toxicity, a formulation for controlling plant health including the same, and a method of increasing plant health and yields.

To achieve the above objective, disclosed embodiments provide a formulation for increasing plant health containing kelps at a concentration of 5-7 percent plus proplis at 2-4%.

In some embodiments, the above formulation may include fertilizers that are both chelated with IDHA or Fulvic acid allowing for both conventional and organic labeling In disclosed embodiments, the volume ratio of the fertilizers and the propolis may be 2:1 to 6:1 based on the same concentration.

Propolis is a natural resinous mixture produced by honey bees from substances collected from parts of plants, buds, and exudates. Due to its waxy nature and mechanical properties, bees use propolis in the construction and repair of their hives for sealing openings and cracks and smoothing out the internal walls and as a protective barrier against external invaders like snakes, lizards, and so forth, or against weathering threats like wind and rain. Bees gather propolis from different plants, in the temperate climate zone mainly from poplar. Current antimicrobial applications of propolis include formulations for cold syndrome (upper respiratory tract infections, common cold, and flu-like infections), wound healing, and treatment of burns, acne, herpes simplex, and neurodermatitis.

Since ancient times propolis has been extensively employed by man, especially in folk medicine to treat several maladies. Egyptians used bee glue to embalm their cadavers as they well knew about its putrefactive properties. Incas employed propolis as an antipyretic agent. Greek and Roman physicians used it as a mouth disinfectant and as an antiseptic and healing product in wound treatment, prescribed for topical therapy of cutaneous and mucosal wounds.

Nowadays, propolis is a natural remedy found in many health food stores in different forms for topical use. It is also used in cosmetics or as a popular alternative medicine for the self-treatment of various diseases. Current applications of propolis include formulations for cold syndrome (upper respiratory tract infections, common cold, and flu-like infections), as well as dermatological preparations useful in wound healing, treatment of burns, acne, herpes simplex and genitalis, and neurodermatitis. Propolis is also used in mouthwashes and toothpaste to prevent caries and to treat gingivitis and stomatitis. It is widely used in cosmetics and in health foods and beverages. It is commercially available in the form of capsules, mouthwash solutions, creams, throat lozenges, powder, and also in many purified products from which the wax was removed. Due to its antimicrobial, antiviral, and antioxidant properties, it can also be utilized for a longer flower hold with disclosed compisitions herein.

Propolis is a complex mixture made by bee-released and plant-derived compounds. In general, raw propolis is composed of around 50% resins, 30% waxes, 10% essential oils, 5% pollen, and 5% of various organic compounds. More than 300 constituents were identified in different samples and new ones are still being recognized during the chemical characterization of new types of propolis. The proportions of the various substances present in the propolis depend upon its place and time of collection.

Many analytical methods have been used for the separation and identification of propolis constituents and the substances identified to belong to the following groups of chemically similar compounds: polyphenols; benzoic acids and derivatives; cinnamic alcohol and cinnamic acid and its derivatives; sesquiterpene and triterpene hydrocarbons; benzaldehyde derivatives; other acids and respective derivatives; alcohols, ketones, and heteroaromatic compounds; terpene and sesquiterpene alcohols and their derivatives; aliphatic hydrocarbons; minerals; sterols and steroid hydrocarbons; sugars and amino acids. As it may be expected, volatile compounds (produced by the source plants) are present in low amounts. Sugars are thought to be introduced accidentally during the elaboration of propolis and/or the passage of bees over the resin. Some compounds are common in all propolis samples and determine their characteristics and properties.

Considering the complex structure of propolis, it cannot be used directly. Propolis is extracted commercially with a suitable solvent. The most common solvents used for extraction are water, methanol, ethanol, chloroform, dichloromethane, ether, and acetone. Many of the bactericidal components are soluble in water or alcohol which should remove the inert material and preserve the desired compounds. Propolis composition depends upon the geographical region and the second method of extraction, the solvent should be carefully chosen.

The antioxidant activity of Indian propolis extract and its chemical constituent's pinocembrin and galangin. In all the antioxidant assay systems, the aqueous extract of propolis (AEP) showed higher activity compared to the ethanolic extract of propolis (EEP). This may be due to its higher polyphenols content. So, AEP can be a good substitute of ethanol extract. Moreover, it can be used in prevention of various free radical-related diseases. Galangin also showed comparable activity with that of AEP and EEP and highest activity than pinocembrin. This is due to structural differences between these two compounds.

Propolis has also shown fungicide effects on juice spoilage fungi *Candida famata, C. glabrata, C. kefyr, C. pelliculosa, C. parapsilosis*, and *Pichia ohmeri*; the fungicidal effect was associated with the presence of flavonoids. Propolis is the bee product with the highest antifungal activity as tested with 40 yeast strains of *C. albicans, C. glabrata, C. krusei*, and *Trichosporon* spp. Propolis inhibited the growth *C. albicans* (MIC 0.2-3.75 μg/mL), *C. glabrata* (MIC 0.03-7.5 μg/mL), *Trichosporon* spp. (MIC 0.1-0.4 μg/mL), and *Rhodotorula* sp. (MIC <0.01 μg/mL) and the most sensitive strain was *Rhodotorula* spp. The most resistant strain was *C. Albicans*. In an unpublished study in Bangalore, Indian propolis has been observed to be more effective than routinely used anticaries agents in inhibiting the growth of *Streptococcus mutans* which is a frequent cause of dental caries. Oliveira et al. (2006) studied the 67 samples of yeasts isolated and identified from samples of onychomycosis comprising the following species: *Candida albicans, Candida parapsilosis, Candida tropicalis, Candida kefyr, Candida guilliermondii, Candida lusitaniae, Candida glabrata, Candida stellatoidea, Candida Trichosporon* sp. including *T. asahii. T. ovoides*, and *T. cutaneum*, one *Geotrichum candidum*, and three *Saccharomyces cerevisiae. Trichosporon* sp. was the most sensitive species, showing MIC50 and MIC90 of 1.25×10-2 mg/mL of flavonoids, and *Candida tropicalis* was the most resistant, with CFM50 of 5×10-2 mg/mL of flavonoids and MFC90 of 10×10-2 mg/mL. The activity of ethanolic extraction of propolis was elevated by disc diffusion method when the concentration increased to 20% and 30%. EEP was not effective against *C. albicans*.

The disc diffusion method is one of the most popular methods used to determine antimicrobial activity. A suspension of a sensitive indicator microorganism is inoculated on agar plates by spreading homogeneously on its surface, and blank paper discs containing the sample to be checked for antimicrobial activity are placed on top. After an incubation period at optimal temperature, antibacterial activity is evaluated by determining the diameter of the growth inhibition zones in the agar layer surrounding the disc. Some authors argue that this laborious method is unreliable for comparing bioactivities, as results are influenced by the solubility and hence the diffusivity of the individual constituents in agar, proposing the use of another methodology which is also commonly used for the same purpose, the dilution method. In this procedure, propolis samples are serially twofold diluted and a fixed volume is added to a liquid or solid medium, by making a series of concentrations.

Bacterial inoculums are added to each experimental condition and the occurrence of growth is analyzed after incubation at optimal conditions. Broth microdilution is considered a good method for rapid and simultaneous screening of multiple samples; for comparing propolis extracts and giving more consistent results, it is a suitable method to be used. Additionally, it allows the determination of the minimal inhibitory concentration (MIC) and the minimal bactericidal concentration (MBC) which are, respectively, the lowest concentration that inhibits visible bacterial growth and the lowest concentration that kills bacteria. Briefly, thin-layer chromatography plates where propolis samples were eluted are covered with agar suspensions of the microorganism whose sensitivity is going to be tested. Antibacterial activity is visualized as clear areas after proper incubation.

In addition, some embodiments provide a formulation for controlling the plant's metabolism, including the above composition as an active ingredient.

In addition, some embodiments are configured to provide a method of supporting the plant's growth and development, including providing up to 25 percent longer flower hold with the above composition.

In the development of disclosed embodiments, 10 types of plant-derived biological materials were assessed for plant health activity.

In the development of disclosed embodiments, plant health activity on all plants was assessed using fertilizers, propolis, cytokinin, gibberellins, auxins, abscisic acid, brassinosteriods, fucoxanthin, jasmonic and salicylic acid and kelp. Based on the results, superior plant health activity was confirmed when propolis was utilized alone or in combination with kelp and bio-extracts. In particular, when kelp and gibberellic acid were used at 200 to 23000 ppm, superior plant health support was demonstrated without plant toxicity.

Kelps are large seaweeds in the order Laminariales that form dense canopies in temperate rocky intertidal and subtidal habitats less than 30 m in depth. Kelps are characterized by a highly dimorphic lifecycle consisting of a large diploid sporophytic (bed-forming) phase and a microscopic haploid gametophytic phase. Both form conspicuous floating canopies or kelp beds. Sporophytes of Nereocystis are annual or semi-annual, whereas sporophytes of Macrocystis are perennial, persisting for several years. In addition to these dominant bed-forming taxa, numerous species of understory (non-floating) kelp occur in subtidal habitats.

Kelps are important primary producers. They contribute to food webs by providing food for herbivores and detritivores, and by releasing dissolved organic carbon. In addition, kelps create important biogenic habitat that is utilized by fish, invertebrates, marine mammals, and birds. Kelp can significantly alter the physical environment by modifying current and wave energy and this buffering capacity can influence the ecology of other organisms that utilize kelp environments for larval dispersal and settlement, for example, rockfish.

The extent and composition of kelp beds vary through time in response to natural and human-induced influences. In general, the distribution of kelp is determined by the amount of light available for photosynthesis, nutrient levels, grazers, physical disturbances, and toxic contaminants. In addition to these external factors, a demographic structure may play an important role in driving temporal dynamics of Macrocystis kelp beds through decreased fitness of older, more inbred populations.

Therefore, some embodiments pertain to a formulation for increasing plant health and pollination containing propolis at a concentration of 200 to 3,000 ppm.

The propolis is contained in beehives and can be utilized without constraint as to the source material.

In some embodiments, the plant pollination activity may become insignificant if the quantity of propolis in the composition is less than 100 ppm.

In some embodiments, the formulation for supporting plant health may exhibit superior plant health activity even when containing Kelp alone. To demonstrate a higher and more stable plant metabolic efficiency, multiple bio-fertilizers were selected consisting of fertilizers, propolis, cytokinin, gibberellins, auxins, abscisic acid, brassinosteroids, fucoxanthin, jasmonic and salicylic acid and kelp may be added. Here, the volume ratio of the extracts and the propolis is preferably 2:1 to 4:1 based on the same concentration.

The extracts may be acquired using a process selected from the group consisting of typically known extraction processes, such as alcohol extraction, hexane extraction, hot-water extraction, hypersonic distillation, CO2 distillation, cold-water extraction, cold compression (expression), and steam distillation.

In some embodiments, the composition for controlling plant health may be used alone but is not particularly limited to that and may additionally include a suitable diluent or excipient depending on the dosage form or use purposes formulation. As the excipient, a typical material may be used depending on the dosage form. When composed, a filler, an extender, a wetting agent, a disintegrant, or a surfactant may be incorporated. Typical examples of the diluent or excipient may include water, dextrin, calcium carbonate, lactose, propylene glycol, amino acid, liquid paraffin, and normal saline. More preferably, secondary distilled water added with 0.1 ml of Triton X-100 per liter (L) is used.

Some other embodiments pertain to a formulation for controlling plant health, including the formulation for controlling plant health as an active ingredient, and to a method of controlling plant health including controlling plant health using the composition for controlling plant health.

In some other embodiments, floral display size and flower color in attracting bee species and relationships between plant attractiveness (number of pollinator visits) may be an important factor to consider.

The ability to attract pollinators is crucial to plants that rely on insects for pollination and subsequent seed set. Various plant traits are known to influence pollinator attraction, including floral display size and flower color. Larger floral displays or inflorescences with more open flowers usually increase pollinator visitation, and greater visitation can augment pollen receipt and seed set. Pollinators often visit more flowers, although a smaller proportion of total flowers, on plants with larger flowers. In hermaphroditic plants, floral display size can serve as a proxy for pollinator resource availability, and this seems to hold true for both pollen and nectar rewards.

Moreover, besides being attracted to larger floral displays, bumble bees can also detect the number of rewarding flowers on an inflorescence. When nectar is the reward, both floral display size and reward are important, and inexperienced bees are attracted to larger floral displays and then learn to respond to a number of flowers with a reward. When pollen is the reward, bumble bees can visually determine the number of pollen-rewarding flowers and select inflorescences with more pollen-rewarding flowers rather than flower display size.

During the development of some embodiments, it is observed that floral display size augmented plant attractiveness to all bee species, but some bee species reacted differently to flower color. Similar plant traits were responsible for both an increase in the probability of a plant not being visited and the number of pollinator visits received by a plant. The two methods of quantifying flower color often affected the results, and the reason for discrepancies between color models may require further testing. Increasing the number of pollinator visits increased the total seed set. However, the slopes of the relationship between pollinator visits and female reproductive success differed among bee species and could be explained by differences in tripping rate or pollinator effectiveness.

These compositions may include the use of Pyroligeneous Acid, Gibberellins 3, and/or Gibberellins 9. Some formulations may also perform well with the use of conjugate bases of these ingredients. Other phytohormones may also be used in the formulation. These ingredients may be obtained in any method including extraction and isolation of the active ingredient from *Gibberella fujikuroi* or other fungus or bacteria.

XV. OTHER APPLICATIONS

Disclosed herein are a set of examples that aim to provide a better understanding of the present invention will be given through the following examples. These examples are merely set forth to illustrate the present invention and are not to be construed as limiting the scope of the present invention, as will be apparent to those skilled in the art.

In some embodiments, the nematodes used in the experiments were mainly *Meloidogyne* spp. The below disclosed experiment results are related to the evaluation of nematocidal activity of naturally derived material.

The tomato roots infected with root-knot nematodes were washed with running water and were then cut to a size of about 1 cm, after which 50 g of the cut roots were placed in a 500 ml round-bottom flask containing 200 ml of 0.5% sodium hypochloride (NaOCl), stopped with a rubber stopper, and shaken vigorously for 3 min to sterilize the roots and at the same time burst the egg bag. Thereafter, the solution was passed through a sieve in which 200 mesh was superimposed on 500 mesh, and washed with distilled water, so the eggs of the root-knot nematodes from which the NaOCl solution was removed were recovered.

Next, the eggs of the root-knot nematodes thus recovered were surface-sterilized with 0.5% NaOCl for 10 min, washed thoroughly with sterile distilled water, placed in a phosphate buffer (1%) containing sterilized normal saline, and hatched in an incubator at 25° C.

Each of geraniol azadirachtin (available from United Agro Industries), clove oil, oregano oil, pyrethrin and oxymatrine was mixed with an emulsifier (PLE9) at 1:1. Thereafter, each mixed solution was diluted to 2000 ppm, 2 to 3 ml thereof was poured into a Petri dish, after which 15 hatched root-knot nematodes were placed in the Petri dish, and nematocidal activity was measured and the results thereof are shown in Table 1 below.

TABLE 1

| Classification | Geraniol | Azadirachtin | Clove oil | Oregano oil | Pyrethrin | Oxymatrine |
|---|---|---|---|---|---|---|
| 1 day | 15[a] | 7 | 2 | 1 | 5 | 7 |
| 2 days | — | 8 | 5 | 1 | 6 | 9 |
| 3 days | — | 10 | 7 | 3 | 11 | 10 |
| Nematocidal efficiency (%) | 100 | 66.7 | 46.7 | 20.0 | 73.3 | 66.7 |

As is apparent from Table 1, the 2,000 ppm geraniol dilution solution exhibited 100% nematocidal efficiency on root-knot nematodes 1 day after treatment therewith, whereas the oregano oil killed 3 root-knot nematodes 3 days after treatment therewith and thus exhibited 20.0% nematocidal efficiency, which is evaluated to be the lowest nematocidal activity.

Therefore, it was determined that geraniol, among the test samples, had the best nematocidal effect on root-knot nematodes, and nematocidal activity was measured depending on the geraniol dilution factor. The results thereof are shown in Table 2 below.

TABLE 2

| Duration | Geraniol (ppm) | | | | | | | |
|---|---|---|---|---|---|---|---|---|
| | 10,000 | 3,000 | 2,000 | 1,000 | 500 | 333 | 200 | 100 |
| 1 day | 15[a] | 15 | 15 | 10 | 5 | 5 | 5 | 5 |
| 2 days | — | — | — | 15 | 10 | 6 | 7 | 7 |
| 3 days | — | — | — | — | 15 | 15 | 13 | 7 |
| Nematocidal efficiency (%) | 100 | 100 | 100 | 100 | 100 | 100 | 86.7 | 46.7 |

The number of root-knot nematodes used for the experiment on the number of killed root-knot nematodes was 15 at each dilution factor.

As is apparent from Table 2, the 10,000 ppm, 3,000 ppm and 2,000 ppm geraniol exhibited 100% nematocidal efficiency on root-knot nematodes 1 day after treatment therewith, and the 1,000 ppm geraniol exhibited 100% nematocidal efficiency 2 days after treatment therewith.

Moreover, the 500 ppm and 333 ppm geraniol exhibited 100% nematocidal efficiency 3 days after treatment therewith, and the 200 ppm geraniol exhibited high nematocidal efficiency of 86.7% 3 days after treatment therewith, based on which the possibility of controlling root-knot nematodes thereby was confirmed.

Below is a discussion of experiment results of phytotoxicity of geraniol oil on various crops.

Sterilized soil was uniformly mixed, 300 g thereof was then placed in each pot, and tomato seedlings not infected with root-knot nematodes were transplanted thereto. 50 ml of each of the geraniol dilution solutions (100, 200, 330, 500, 1,000, 2,000, 3,000, and 10,000 ppm) prepared in Example 1 was used for drenching treatment. Additionally, geraniol dilution solutions at 4,000 ppm, 5,000 ppm, and 20,000 ppm were further prepared, and then 50 ml of each was used for drenching treatment of each pot planted with tomato seedling. Here, the same amount of distilled water was used alone in an untreated group, and 1 week after treatment, the presence or absence of phytotoxicity was observed with the naked eye.

TABLE 3

| Geraniol concentration (ppm) | Test crop | Extent of phytotoxicity (0-5) | Phytotoxicity symptom |
|---|---|---|---|
| 100 | Tomato | 0 | No |
| 200 | | 0 | No |
| 330 | | 0 | No |
| 500 | | 0 | No |
| 1,000 | | 0 | No |
| 2,000 | | 0 | No |
| 3,000 | | 0 | No |
| 4,000 | | 5 | Withered |
| 5,000 | | 5 | Withered |
| 10,000 | | 5 | Withered |
| 20,000 | | 5 | Withered |

As is apparent from Table 3, upon treatment with geraniol at different concentrations, there were no particular phytotoxicity symptoms before or after treatment in the concentration range of 100 ppm to 3,000 ppm. However, at 4000 ppm or more, it was observed that the bottoms of the stems dried up and all tomato seedlings collapsed and withered. Therefore, it was confirmed that geraniol had no effect on tomato seedlings at concentrations of 3,000 ppm or less. but geraniol at concentrations of 4,000 ppm or more caused phytotoxicity in tomato seedlings, making it impossible to use.

The nematocidal activity of palmarosa oil, which is a complex, was confirmed, but there is no description of what compounds exhibit substantial nematocidal activity, among compounds such as dihydrotagetone, thiophene, ocimene, linalool, thymol, estragole, geraniol and the like, constituting palmarosa oil. However, it was confirmed in the present invention that the material that shows substantial nematocidal activity among the compounds constituting palmarosa oil is geraniol, and the use of geraniol alone has a superior nematocidal effect about 4.2 times as high as that of palmarosa oil containing the same amount of geraniol. Furthermore, the present invention is significant in that the concentration of geraniol that can exhibit the maximum nematocidal effect without causing phytotoxicity was found to be 100 to 3,000 ppm.

XVI. LOTION FOR REPELLING OF MOSQUITOS AND CHITOSAN CAPSULATION

Certain formulations may be blended into lotions, sun tanning materials, sprayable insect repellants, or others to form a homogenous mixture or emulsion. Some embodiments may contain a heterogenous mixture or emulsion.

Some embodiments may include chitosan encapsulation of certain formulations. Chitosan is the ideal encapsulation polymer due to its abundance in nature and biodegradability, as well as surface functional groups providing free NH2 groups. The presence of these NH2 groups gives the opportunity to attach functionalized molecules to the chitosan surface for multifunctional applications. To further enhance its ionic character, its free amino groups can be quaternized under acidic conditions. Not only does the cationic nature of chitosan interact with negatively charged bacterial membranes to promote antibacterial activity, but the nanoscale size boosts its antibiofilm properties. Researchers have used chitosan nanoparticles as a method to encapsulate biocides and other natural phytochemicals in order to combat biofilm-based secondary infections. This paper summarizes various carbohydrate-derived biopolymers as antibiofilm materials, with particular focus on chitosan nanoparticles that are used to encapsulate various essential oils, including basil (*Ocimum basilicum*), mandarin (*Citrus reticulata*), *Carum copticum* ("Ajwain"), dill (*Anethum graveolens*), peppermint (*Mentha piperita*), green tea (*Camellia sinensis*), cardamom, clove (*Eugenia caryophyllata*), cumin (*Cuminum cyminum*), lemongrass (*Cymbopogon commutatus*), summer savory (*Satureja hortensis*), thyme, *cinnamomum* (*Cinnamomum zeylanicum*) and nettle (*Urtica dioica*). In addition, chitosan nanoparticles can be used for encapsulating oil-in-water nanoemulsions of *eucalyptus* oil (*Eucalyptus globulus*) and mandarin essential oil, electrospun collagen hydrolysate nanofibers with lemon balm (*Melissa officinalis*) and dill (*Anethum graveolens*) essential oil, carvacrol and cinnamaldehyde components, and other natural and synthetic oils.

Chitosan capsulation may pose as potential method to reduce the environmental impact of pesticides. Naturally derived chitosan is a biopolymer derived from the shells of crustaceans that has been shown to have a variety of applications in the field of agriculture. Chitosan can be used to encapsulate pesticides, allowing for controlled release over an extended period of time. This can reduce the amount of pesticide needed, as well as minimize the amount of pesticide that leaches into the environment. Other benefits of chitosan capsulation include increased efficacy of pesticides, improved transport and storage, and reduced toxicity. Chitosan capsulation has been successfully used to encapsulate a variety of pesticides, including insecticides, fungicides, and herbicides. Some embodiments may include the synthetic production of chitosan instead of the extraction of chitosan from certain organisms such as crustaceans, fungi, insects, algae, microorganisms, or other organisms. Some embodiments may include the production of chitosan from the treatment of chitin with alkaline compounds.

Demineralization deproteinization and discoloration of animal shells/exoskeletons such as lobsters and crickets to obtain chitin. Deacetylation of the chitin to create chitosan for use in adsorption of essential oils and other active ingredients. The deacetylation process is a process of hydrolysis of acetamide groups in chitin using NaOH solution at high temperatures to produce amino groups in chitosan.

Figure 5:
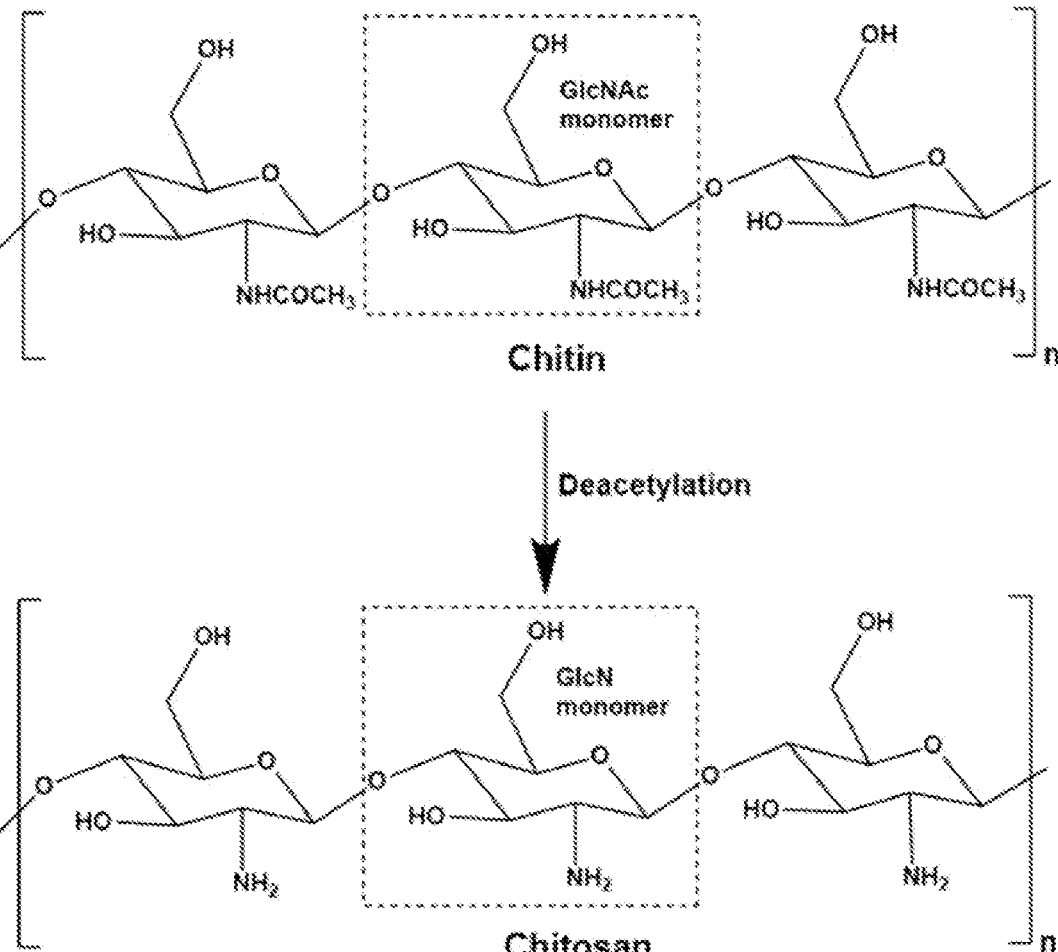
FIG. 5 is a figure showing the deacetylation reaction of chitin into chitosan.

N-Acetylglucosamine (GlcNAc) is the monomeric unit of the polymer chitin, the derivative of chitosan. GlcNAc is a monosaccharide that usually polymerizes linearly through $(1,4)$-$\beta$-linkages, these linkages create chitin in the form of a polymer. Glucosamine (GlcN) is th monomer of chitosan. FIG. 5 shows the Deacetylation of chitin into chitosan. The reaction removes an acetyl group (COCH3) from the amide group (NHCOCH3) on chitin to create the primary amine (NH2) found in chitosan. This allows chitosan to act as an amphiphilic molecule and surround non-polar molecules (such as essential oils) while staying suspended in water or other polar solvents. This also helps to create a stable emulsion.

The process of chitosan capsulation involves encapsulating drugs in a shell consisting of chitosan and other carriers such as polyalcohols and polysaccharides. This method has several advantages including increased solubility, controlled release, and biocompatibility. Additionally, chitosan biodegrades safely in the body and is non-toxic, making it a desirable alternative for drug delivery. Studies have shown that chitosan capsules are highly effective at delivering drugs to the affected area, often with better results than traditional methods. The normal application of use for chitosan capsulation includes drug targeting at the cellular level. Some embodiments may use chitosan capsulation as a bug and pest deterrent instead of the normal application of use. Some embodiments may also be used on pesticide formulations to allow for the penetration of bug-repellant formulations into the plant passed the cuticle and epidermis cells to allow for controlled release and long-lasting application of pesticides.

Certain applications may control ants, snails, slugs, roaches, crickets, locust, pincher bugs, mosquitos, fungi, nematodes, bacteria, larvae, and other pests with encapsulations using chitosan. Certain formulations may include use with fertilizers to bypass Chitin Elicitor Receptor Kinase 1 (CERK1) and increase absorption. This allows materials to be carried deeper into the plant while reducing fertilizer load and energy used to convert and absorb the composition.

Chitin Elicitor Receptor Kinase 1 (CERK1) is a protein that is a key component of the chitin recognition pathway in plants. It is a receptor-like kinase (RLK) that functions as a receptor for chitin. CERK1 is essential for plants to activate the defense response against pathogens by recognizing the presence of chitin. It does this by binding to chitin molecules and initiating a signaling cascade that leads to the production of defense-related proteins. CERK1 is involved in the regulation of several processes including defense against fungal pathogens, root nodule formation, and plant hormones.

Chitosan capsulation may wrap into mined layers allowing for them to work over a period of time and still work effectively when in contact with either polar or non-polar substances such as water or oil. Chitosan capsulation also works on a secondary aspect of being safe for humans allowing for the mosquito (and other pests) repelling materials to be blended into lotions and or sun tanning materials. With this, they lock into Dermis layer of the skin allowing for longer water stability. This will the formulations the ability to last up to 20 hours even after swimming for repelling mosquitos. Some embodiments may allow the formulations to last up to 48 hours.

Chitosan also allows materials to be wrapped onto or impregnated with fertilizers/humates and fulvics for seed coatings. Some embodiments may package materials in a water soluble packaging (WSP) pack material, decreasing shipping costs and increasing the storability of botanical materials. In some embodiments, this can be installed in a fulvic pack providing Pyroligneous acid load for the plant. Certain embodiments may also include chitosan-based fertilizers in combination with other formulations to produce a pesticide/fertilizer multiuse product. These products may also contain fulvic acid, bentonite, urea, and/or water in addition to any prementioned formulations such as the ones containing oxymatrine, geraniol, and other natural and synthetic oils. In some embodiments, these formulations may be mixed and emulsified to create a homogenous formulation. The WSP pack may also allow for a significant reduction of chemical exposure to handlers.

Some embodiments may contain a solid formulation or highly concentrated formulation to be mixed with water or other liquid by the consumer after purchase. This may allow for a product to be manufactured, shipped, and sold for a lower cost because less space is needed for the product. This may also help decrease packaging costs and environmental waste.

XVII. NEUROTRANSMITTER INHIBITION

The nervous system is made up of neurons and has the role of gathering information from the environment, processing it, and using it to modify behavior. The system receives stimuli through sensory neurons, which convert the stimuli into electrical signals called action potentials. These signals travel in a single direction along the neuron membrane, towards a synaptic cleft, which is the junction between two neurons. At the synaptic cleft, the action potential causes the release of neurotransmitters that can either excite or inhibit the next neuron.

The nervous system is critical for animal (and insect) function and is therefore a highly susceptible target for toxic substances. Pesticides can interfere with the movement of stimuli along the neuron membrane and the chemical transmission to another neuron or cell. All living cells have a transmembrane electrical potential, and neurons use this to transmit the stimulus. The transmembrane electrical potential is generated by the distribution of different ions, and the ionic pump uses energy from ATP to maintain the charge imbalance across the membrane. In a resting neuron, sodium and potassium ions are asymmetrically distributed across the membrane, making the inside negative compared to the outside. This is due to the exchange of about 2 potassium ions into the membrane for every 3 sodium ions out of the membrane. This causes polarization in the neuron membrane.

The nerve excitability is due to the ability of the membrane to temporarily change in response to external stimuli, and this is caused by inward and outward currents of sodium and potassium ions. The action potential moves in one direction along the axon as a wave of depolarization. In the central nervous system, neurons communicate chemically through synapses, which are specialized junctions. The electrical signal is converted into a chemical signal at the synapse, which is received by other nerves or muscles. Chemical transmission is initiated by an action potential causing depolarization. Excitatory and inhibitory neurotransmitters have been identified in synapses, and in excitatory synaptic transmission, the wave of depolarization reaches the synaptic region, causing voltage-gated calcium ion channels to open and allowing the inward movement of calcium ions.

One key aspect of insect nervous system function is the release of neurotransmitters, such as acetylcholine, into the synaptic cleft. The presence of increased calcium ions within the neuron triggers the exocytosis release of these chemicals. Once released, the acetylcholine molecules randomly diffuse within the synaptic cleft, with random chances of encountering either the acetylcholinesterase enzyme or the acetylcholine receptors. If a molecule binds with the enzyme, it is broken down into choline and acetate, which are reabsorbed and used to create new acetylcholine molecules. On the other hand, if the molecule binds to a receptor site, it causes depolarization of the postsynaptic membrane, leading to the transmission of a nerve impulse along the axon.

Inhibitory synaptic transmission works in a similar manner, with the main difference being the involvement of the GABA receptor. This receptor acts as the primary inhibitor at the insect neuromuscular synapse, and when the inhibitory neurotransmitter GABA binds to it, chloride ion channels open, causing an inward movement of chloride ions into the neuron membrane. This increase in conductance leads to hyperpolarization of the membrane and the blocking of excitatory stimuli.

Insecticides are often developed with the goal of disrupting the functioning of the nervous system. For example, some insecticides interact with sodium channels by either keeping them open, leading to repetitive discharge and excitation, or keeping them closed for a longer period, resulting in depression. Others interfere with acetylcholine by either binding to acetylcholinesterase and preventing acetylcholine binding, leading to more frequent binding with receptors and increased excitation, or by binding to acetylcholine receptors themselves and blocking the effect of acetylcholine, resulting in paralysis and inhibition of impulse propagation across the synapse.

Similarly, insecticides can also act on GABA receptors and transmitters. For instance, GABA antagonists inhibit the effects of GABA, leading to excitation, while GABA agonists increase the affinity of the receptor for GABA, leading to depression. These insecticides exploit the fact that GABA acts to increase chloride conductance and hyperpolarize the membrane, and inhibition of this effect leads to excitation.

The nervous system plays a crucial role in the functioning of animals by gathering information from the environment, processing it, and modifying neural programs to result in behavioral performance. It consists of neurons and is a complex network of communication pathways that transmit information between different parts of the body. The system is highly sensitive to poisons, and this sensitivity makes it an important target for pesticides.

The nervous system receives input in the form of a stimulus that is captured by a sensory neuron. The stimulus energy is transduced into an electrical signal, also known as an action potential, which travels in one direction along the neuron membrane towards the synaptic cleft. the junction between two neurons. At the synaptic cleft, the action potential triggers the release of neurotransmitters, which can either be excitatory or inhibitory in nature.

The transmembrane electrical potential is an important aspect of the nervous system and is generated by a controlled distribution of different ions, with energy from ATP used to transmit the stimulus. An ionic pump creates a charge imbalance across the membrane by carrying sodium ions out of the neuron and potassium ions into the neuron, leading to a polarized state.

In response to external stimuli, the neuron membrane undergoes transient changes in membrane potential, which are caused by inward and outward currents of sodium and potassium ions, respectively. A stimulus to the neuron results in an action potential that moves along the axon in one direction as a wave of depolarization. The opening of sodium ion channels causes a sharp increase in inward sodium ion movement, leading to a rapid change in potential differences across the membrane and a decrease in sodium conductance by closing sodium ion channels.

Gamma-aminobutyric acid (GABA) is an amino-acid neurotransmitter that primarily acts as an inhibitor in the nervous system and muscles of both mammals and insects. However, in certain instances, it can also function as an excitatory neurotransmitter. It binds to specific receptors, known as GABArs, in both synaptic and extrasynaptic membranes. GABA blocks specific signals in the central nervous system.

Acetylcholine is an excitatory neurotransmitter that acts to initiate a response in the cell. It plays a vital role in muscle control, autonomic functions, and memory. Acetylcholine receptors are a class of protein molecules located on the surface of nerve cells and muscle cells. There are two main types of acetylcholine receptors: nicotinic receptors, which are found in both nerve and muscle cells, and muscarinic receptors, which are found primarily in nerve cells. These receptors bind acetylcholine to initiate a cellular response in neurons or muscle cells. In muscle cells, the binding of acetylcholine to nicotinic receptors causes muscle contraction. In the nervous system, the binding of acetylcholine to muscarinic receptors modulates the activity of other neurotransmitters and affects various physiological processes such as heart rate, breathing, and memory formation.

Insecticides that inhibit the GABA and acetylcholine neurotransmitters can interfere with the normal functioning of the nervous system. GABA is an inhibitory neurotransmitter that slows down nerve impulses and helps regulate muscle tone. Acetylcholine is an excitatory neurotransmitter that is involved in many physiological processes, including muscle contraction, learning, and memory. Insecticides that target these neurotransmitters can cause a range of adverse effects, including paralysis and death, in the insects they are meant to control. In some embodiments, active ingredients may bind to acetylcholine receptors and block acetylcholine from being transmitted through neurons. This may induce paralysis. In some embodiments, active ingredients may bind to GABA receptors and block GABA from being transmitted through neurons, this may induce muscle spasms and seizures.

Action potentials are rapid sequences of changes in the voltage across the membrane of a neuron. Sodium and potassium channels open and close based on the depolarization of the membrane and the outside of the membrane.

When GABA reacts with the receptors of a neuron, it blocks the neuron from firing an action potential or releasing neurotransmitters. When GABA binds to GABArs on a neuron, it allows Cl-to permeate into the neuron which decreases the probability for the neuron to fire an action potential. Some pesticides may take advantage of GABA receptors by blocking GABA from reaching the GABA receptors on a neuron. This can result in muscle spasms or seizures due to an increased flow of acetylcholine that is not being inhibited by GABA in the neurons. This eventually leads to the death of the insect.

Neurons communicate across synapses which convert electrical signals to chemical signals excitatory and inhibitory neurotransmitters may be found in synapses.

Some embodiments include an active ingredient that blocks GABA from entering through the GABA receptors. This prevents the inhibition of neurotransmitters and causes an overexcited state in the neurons leading to incapacitation, seizures, or other neurological effects.

GABA (Gamma-aminobutyric acid) is a neurotransmitter found in the central nervous system and muscles of mammals and insects. It primarily acts as an inhibitor by blocking the transmission of excitatory stimuli and neurotransmitters, thereby reducing the likelihood of firing action potentials in neurons. GABA interacts with specific receptors called GABArs, allowing Cl— ions to enter the neuron and further reducing its excitability.

However, in some instances, GABA can also function as an excitatory neurotransmitter. In such cases, blocking the entry of GABA into neurons can lead to an overexcited state, leading to various neurological effects such as seizures or incapacitation. In addition to blocking GABA, active ingredients may also bind to acetylcholine receptors, preventing the transmission of acetylcholine, and inducing paralysis.

In summary, GABA plays a critical role in regulating the excitability of neurons in the central nervous system. Its interaction with GABArs and acetylcholine receptors is a complex process that can have both inhibitory and excitatory effects on neuronal signaling.

GABA (gamma-Aminobutyric acid) inhibiting insecticides are a class of pesticides that target the GABA neurotransmitter system in insects. The GABA system plays a crucial role in regulating the nervous system, and by inhibiting this system, the insect becomes paralyzed and eventually dies. These insecticides work by mimicking the effects of GABA in the insect's nervous system and over-activating the GABA receptors, leading to excessive inhibition and death. Examples of GABA-inhibiting insecticides include neonicotinoids and fipronil. These insecticides are widely used due to their high efficacy and low toxicity to mammals. However, their widespread use has also led to the development of insect resistance, highlighting the need for alternative pest control methods.

GABA-inhibiting insecticides are a class of pesticides that target the GABA neurotransmitter system in insects to control pests such as aphids, whiteflies, *thrips*, termites, and ants. These insecticides have several advantages, including high efficacy, low toxicity to mammals, selective toxicity, long-lasting protection, and reduced use of other pesticides.

One of the advantages of GABA-inhibiting insecticides is their specificity. These insecticides do not affect mammals, birds, or other non-target organisms because their nervous systems do not have the same sensitivity to the effects of GABA.

Myelin allows the action potentials to move at a faster rate through neurons. Insects do not have myelin encasing the axons in their neurons. Because insects are small, the lack of myelin does not affect them in the same way a lack of myelin would affect mammals.

Some embodiments may also include the use of active ingredients that induce cholinesterase inhibition or excitation. These may cause muscle relaxation or muscle paralysis by causing a sodium/potassium imbalance in the neurons of the insect, preventing normal transmissions of action potentials. Some pesticides may also prevent the transformation of choline into acetylcholine. Some embodiments may include active ingredients that induce glutamate inhibition or excitation. Other embodiments may also excite or inhibit other neurotransmitter receptors found in insects.

Some embodiments include specific modes of action used by the pesticidal active ingredients in the formulation, the modes of action may be membrane disruption, substrate deprivation, binding to cell wall complexes, enzyme inactivation, GABA inhibition, acetylcholine inhibition, paralysis, protein binding, inactivation of disulfide bridges, or interaction with eucaryotic DNA.

XVIII. HYPERSONIC DISTILLATION

Centrifugal distillation and extraction are techniques used to extract plant essential oils. Both methods use centrifugal force to separate the volatile components of plants from the non-volatile components.

Centrifugal distillation involves placing the plant material in a rotating drum or basket, which is heated to a specific temperature. As the plant material heats up, the essential oils are vaporized and collected in a condenser. The centrifugal force helps to separate the volatile components from the non-volatile components of the plant, which are left behind in the drum.

One advantage of centrifugal distillation is that it can be used to extract essential oils from a wide variety of plants, including those with a low oil content. It is also a relatively fast method, and it can be scaled up for commercial production.

Centrifugal extraction, on the other hand, involves placing the plant material in a centrifuge and spinning it at high speeds. The force generated by the centrifuge separates the essential oils from the plant material, which are then collected in a container.

One advantage of centrifugal extraction is that it is a more gentle method than other extraction techniques, such as steam distillation. This can be important for plants that are sensitive to heat or pressure. It is also a relatively fast method, and it can be used to extract essential oils from a wide variety of plant material.

Both centrifugal distillation and extraction are used in the production of essential oils for use in aromatherapy, perfumes, and other products. They are generally considered safe methods for extracting essential oils, and they do not leave behind any chemical residues or solvents. However, it is important to use high-quality plant material and to follow proper safety procedures when using these techniques.

Centrifugal distillation and extraction are commonly used in the essential oil industry to extract and isolate the volatile components of plants. The essential oils that are obtained from these methods are highly concentrated, and contain the characteristic aromatic compounds that give each plant its unique scent and therapeutic properties.

In addition to their use in aromatherapy and perfumery, essential oils are also used in a wide range of other applications, such as in the food and beverage industry, for natural cleaning products, and in the pharmaceutical industry.

The quality of the essential oils obtained through centrifugal distillation and extraction is highly dependent on the quality of the plant material used. It is important to use fresh, high-quality plant material that is free from contaminants and has not been treated with pesticides or other chemicals.

Another important consideration is the temperature and pressure used during the extraction process. In general, lower temperatures and pressures result in a higher quality essential oil, as higher temperatures can cause degradation or denaturation of the aromatic compounds.

Centrifugal distillation and extraction are effective and safe methods for obtaining high-quality essential oils from a wide range of plant material. These techniques offer a fast and efficient way to extract essential oils, while minimizing the risk of chemical contamination and ensuring the preservation of the aromatic compounds that make each plant unique.

Some embodiments include the use of a novel centrifugal extraction method herein referred to as "hypersonic distillation". Hypersonic distillation is a special type of centrifugal distillation. It requires less solvent than standard extraction techniques. This allows the essential oils (or absolutes) to be almost solvent-free after extraction without the need for the solvent to be evaporated off. This evaporation process normally takes some of the volatile aromatics with the solvent during this process. With hypersonic distillation, absolute oils can be created without the loss of crucial compounds normally considered volatile. These absolutes are considered stable, and the compounds that are normally volatile are now non-volatile in absolute oils.

This process allows for the creation of non-volatile absolute botanicals (less volatile, more pure essential oils). These do not react with sulfur, so a mixture of the composition with sulfur can provide an effective pesticidal formulation that does not cause burns to plants. This is important as many sulfur-based fertilizers can cause damage to plants if not formulated correctly.

XIX. MULTI-LAYER CHITOSAN ENCAPSULATION

Disclosed herein are systems and methods for multi-layer wrapping of active ingredients in organic polymers. The main organic polymer used for this method is chitosan. This method allows for the encapsulation of any liquid ingredient (whether it be polar, non-polar, or amphiphilic) in chitosan. Preferred embodiments include wrapping nanoparticles of active ingredients in true spheres of chitosan. This can be accomplished by spraying the active ingredients with chitosan and centrifuging at 6000 rps in a centrifugal apparatus. This method allows for perfect nanoparticle spheres to be created. The rps used in the encapsulation method may change from 4000-8000 rps depending on the active ingredient used, its polarity, and its viscosity.

Some embodiments include a method of chitosan encapsulation of pesticidal active ingredients. The method includes adding a first active ingredient to a centrifuge, adding a solution containing chitosan into the centrifuge, centrifuging the chitosan-active ingredient mixture to create nanoparticle spheres of a first diameter, collecting the nanoparticle spheres of a first diameter, adding the nanoparticle spheres, a second active ingredient, and a chitosan solution into a centrifuge, and centrifuging to create nanoparticle spheres of a second diameter larger than the first diameter, and collecting the nanoparticle spheres of a second diameter.

In some embodiments, the first active ingredient is one of an organic essential oil and an organic absolute botanical. In some embodiments, wherein the first active ingredient and the second active ingredient and the same active ingredient. In some embodiments, the first active ingredient is one of plant essential oil and plant extract. In some embodiments, the one of plant essential oil and plant extract is oxymatrine, geraniol, castor oil, castor extract, linseed, cedar, cinnamon, mint, peppermint, citronella, clove, corn, rosemary, cottonseed, sesame, garlic, soybean, thyme, geranium, lemongrass, tea tree, white mineral oil, citrus, spearmint, and a mixture thereof. In some embodiments, the nanoparticle spheres are collected as a solid powder or in a solution. In some embodiments, the nanoparticle spheres of a second diameter have a diameter of 20-200 nm. In some embodiments, the chitosan-active ingredient mixture is centrifuged at 6000 rps to obtain perfect spheres of chitosan-wrapped active ingredient.

Some embodiments include a diluent added to the nanoparticle spheres after the final centrifugation step, the diluent being one of water, dextrin, calcium carbonate, lactose, propylene glycol, liquid paraffin, and normal saline. In some embodiments, the nanoparticle spheres of a second diameter are used in pesticidal compositions. In some embodiments, the nanoparticle spheres of a second diameter are used in one of perfumes, lotions, medical treatments, sunscreens, and insect repellants. In some embodiments, the nanoparticles are collected via a nozzle with an internal portion in the centrifuge, and an external portion outside the centrifuge.

In some embodiments, the diameter of the internal portion of the nozzle is 0.2-0.6 mm and the diameter of the external portion of the nozzle is 0.7-1.0 mm. Some embodiments include adding additional alternating layers of compositions containing active ingredients and layers containing chitosan to the second set of nanoparticle spheres.

Figure 6:
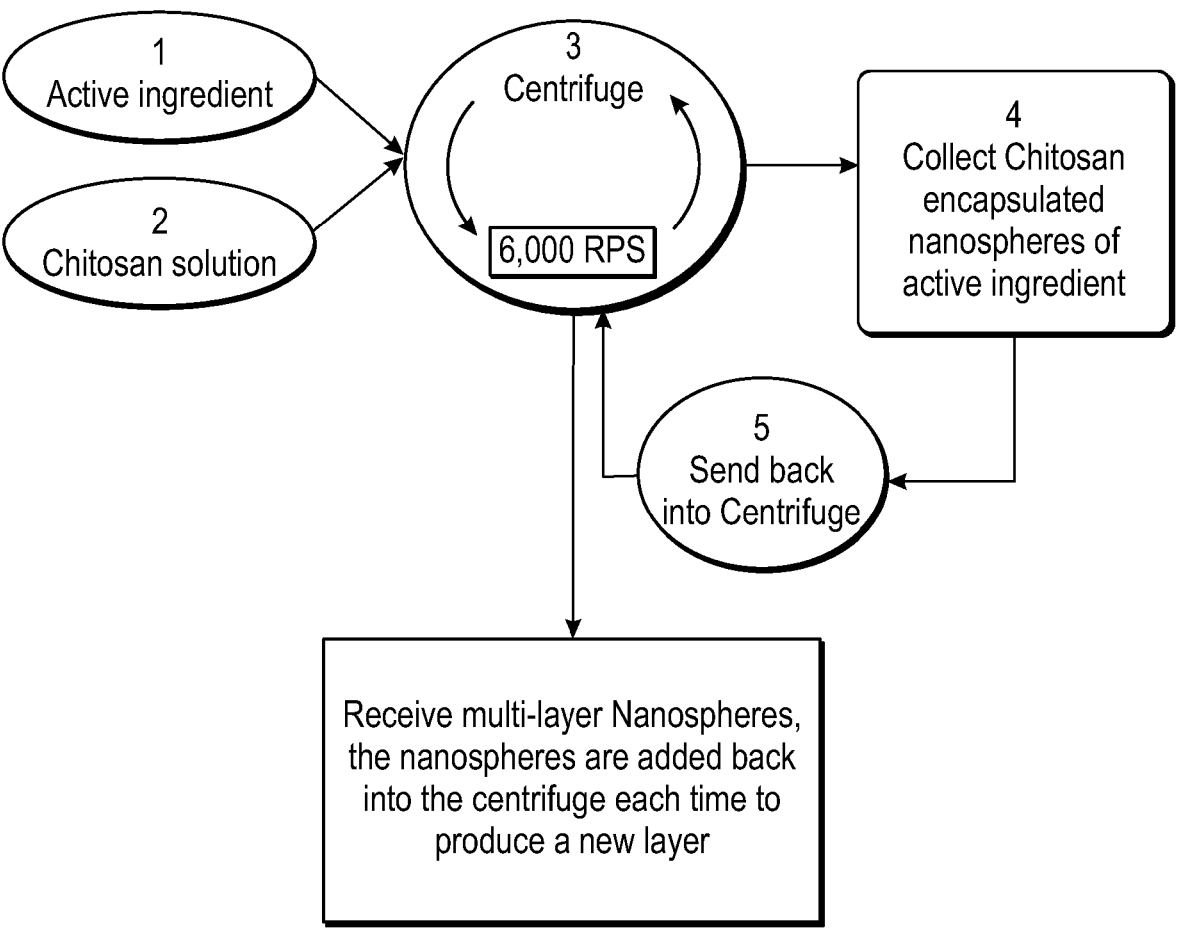
FIG. 6 is a flowchart describing the steps for encapsulating an active ingredient with multiple layers of chitosan.

FIG. 6 is a flowchart describing the steps for encapsulating an active ingredient with multiple layers of chitosan. The active ingredient 1 and the chitosan solution 2 are added to the centrifuge 3 and spun to create an emulsion at 6,000 revolutions per second (rps). The emulsion is collected in the form of nanoparticle spheres through a nozzle 4. The nozzle has an internal portion and an external portion, the internal portion is used to collect the emulsion from the centrifuge, and the external portion of the nozzle is used to release the nanoparticles to be collected. In a preferred embodiment, the internal nozzle is between 0.2-0.6 mm and the external nozzle is between 0.7-1.0 mm in diameter of the opening. Other embodiments may include a smaller nozzle to create smaller nanoparticles, or a larger nozzle to expel the emulsion in a non-nanosphere form. The nanoparticle spheres are added back 6 into the centrifuge with more active ingredient and chitosan solution. The additional active ingredient coats the nanoparticle spheres, and the chitosan wraps that active ingredient to create another layer of active ingredient on each nanoparticle. This is called the "second layering step". These nanoparticles are collected through the nozzle.

In some embodiments, there may be a third layering step, fourth layering step, etc. where the nanoparticles collected after the second layering step are added back into the centrifuge to be coated in another layer of active ingredient and chitosan. The outermost layer must always include chitosan (or another chelating or wrapping ingredient) because when the chitosan degrades, the active ingredient is released. This is useful in many industries such as pesticides, perfumes, insect repellants, sunscreens, etc. In some embodiments, a different active ingredient may be added to the centrifuge in the second layering step (or other steps). The "true"-spherical encapsulation of the active ingredient allows for a large number of stable layers. A multi-layer chitosan encapsulated nanosphere has been created with 128 layers. This was possible because of the chitosan, the specific active ingredient, and the "true"-spherical encapsulation. It would be possible to create a nanosphere with any number of layers (Ex. 10, 20, 100, 1000, etc.) Some embodiments include altering the rps of the centrifugation step depending on the number of layers of the nanospheres being added to the centrifuge. Some embodiments may include using a different centrifuge for each step successive layering step. This would allow for different nozzle sizes to be used without the hassle of replacing the nozzle between each layering step.

Preferred embodiments include wrapping these spheres in more layers of active ingredients and chitosan. These layers will alternate between active ingredient and chitosan, and the method of producing the second layer includes drying the original true spherical nanoparticles Some embodiments may include slightly altering the rps of the centrifuge to create non-"true" spherical encapsulations. This still allows for multiple layers of chitosan and active ingredients, but the amount possible depends on the size of the nano-particles and the number of layers. These non-"true" spheres are not as stable as the "true" spheres and may not deteriorate over the same timeframe, producing a product that is not as effective at slow release. True spheres allow for more layers (currently up to 128, but it would be easy to implement more). Each layer adds to the total diameter of the sphere, but the rps used allows for how thick each layer is. Some embodiments may also include wrapping non-"true" spheres in multiple layers of chitosan.

The active ingredients used may be one of any liquid substance but are preferably one of the aforementioned active ingredients used in the pesticidal formulations/compositions.

Standard practices use non-organic means to create chitosan from chitin. These methods work well, but some pesticides may need organically approved chitosan to provide for organic agriculture. While effective, organic farming may require the use of organically approved chitosan that is created using organic methods. Our approach to chitosan production involves enzymatic extraction, which results in a stable deacetylated chitosan with a purity of 97%. Additionally, we use Pyroligneous acid, which is distilled from wood vinegar using hypersonic cold extraction. This unique process allows us to create a stable chitosan that is suitable for organic agriculture. Any chitosan may be used in the multi-layer wrapping, but organically-derived chitosan is preferred when creating pesticides for organic agricultural use. Some embodiments include a true spherical copolymer encapsulation layer with a 24-hour decomposition breakdown.

The chitosan may be coated in crosslinking agents such as sodium triphosphate pentabasic (STP). The specific crosslinking agent used allows the chitosan to be coded to decompose when specific triggers occur. For example, a specific crosslinking agent may code the chitosan wrap to deteriorate based on pH, polarity, and/or time. In the chitosan is coded for pH, it means that if the chitosan comes in contact with a certain pH, it starts the degrading process. If coded for polarity, it means that if the chitosan comes in contact with a certain solution (such as water, alcohol, or oil) that has the coded polarity, the chitosan will start to degrade. The coding for time is standard, and once administered, the chitosan will slowly degrade over time based on how stable the chitosan wrap is. A more stable wrap will degrade over a slower period of time. A preferred embodiment includes chitosan wraps that degrade about 24 hours per wrap.

Chitosan can also be coded to degrade based on a specific pH, which can be beneficial in targeting pests that thrive in certain pH environments. This coding is achieved by using specific crosslinking agents that are designed to trigger the degradation of the chitosan when it comes into contact with the pH environment of the targeted pest. This specific chitosan is not coded for time, meaning that it will only degrade when in contact with the specific pH and will not degrade in open air. The specific elements used to code for pH degradation may vary depending on the targeted pest and the environment in which it thrives. Some embodiments include chitosan wraps coded to degrade in the presence of a pH specific to a certain fungus. By adjusting the stability of the chitosan at a certain pH level to match that of the fungus, it is possible to code the chitosan to degrade at that specific pH. This means that the chitosan will remain stable and resistant to degradation until it comes into contact with the fungus, at which point it will degrade and release its active components.

Figure 7:
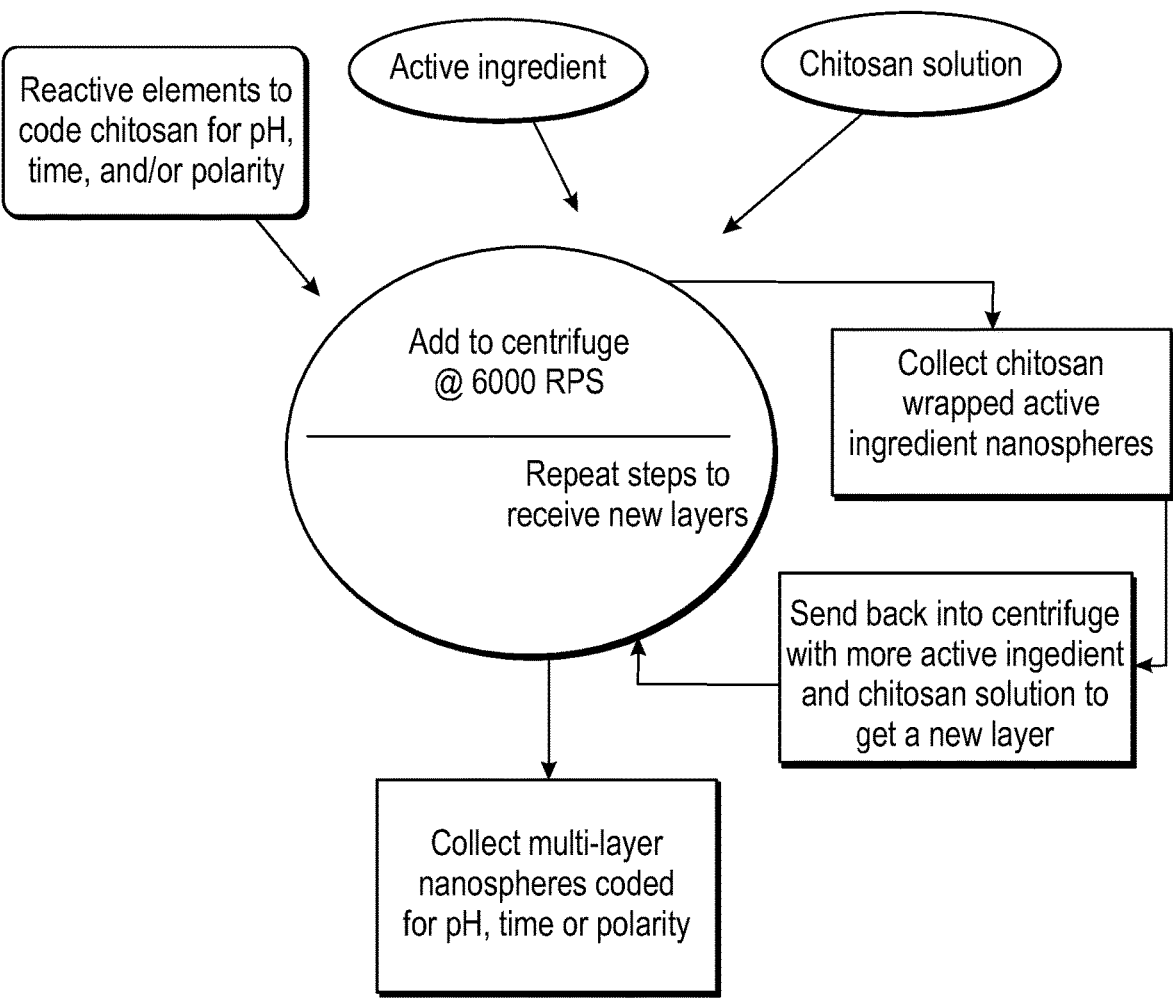
FIG. 7 is a flowchart describing the steps for encapsulating an active ingredient with multiple layers of chitosan and coding the chitosan to break down based on pH, polarity, and/or time.

FIG. 7 is a flowchart describing the steps for encapsulating an active ingredient with multiple layers of chitosan and coding the chitosan to break down based on pH, polarity, and/or time. The active ingredient and the chitosan solution are added to the centrifuge 3 and spun to create an emulsion at 6,000 revolutions per second (rps). The emulsion is collected in the form of nanoparticle spheres through a nozzle. Certain crosslinking agents may be added to the chitosan/active ingredient emulsion to code the chitosan to break down depending on pH, polarity and/or time. One of these crosslinking agents may be sodium triphosphate pentabasic (STP). Some embodiments may include collecting the nanoparticles in a method other than through a nozzle. Each layering step may include the use of a different crosslinking agent to code different layers of the nanospheres for different criteria. For example, layer 1 may be coded to degrade at a pH of 5, but layer 2 may be coded to degrade at a pH of 7. Layers 1 and 2 may also be coded for pH and polarity respectively. Some embodiments include combining the chitosan solution with the crosslinking agent before coming in contact with the active ingredient in the centrifuge. Some embodiments may include adding the chitosan and active ingredient together before adding them to the centrifuge.

This approach has the potential to be a game-changer in the field of agricultural biotechnology, as it could provide farmers with a more natural and sustainable way to protect their crops without relying on synthetic chemicals. Moreover, since the chitosan only degrades in the presence of the specific fungus, it could reduce the risk of unintended environmental harm caused by the release of active compounds into the environment.

Chitosan's unique property of layer-by-layer degradation allows for the slow release of active ingredients in a controlled manner. The crosslinking agents used to coat the chitosan can code it to degrade one layer at a time, typically at a rate of around 24 hours per layer, releasing the encapsulated active ingredients at a controlled rate. This slow release of active ingredients can be beneficial in a variety of applications, including drug delivery, wound healing, and agricultural pesticides. It ensures that the active ingredients remain effective for a longer period of time and reduces the need for frequent application or dosing. This controlled release also minimizes potential side effects and improves the overall safety and efficacy of the product.

The slow release of pesticides using chitosan has several advantages over traditional methods of pesticide application. Firstly, it ensures that the active ingredient is released in a controlled manner, thereby reducing the risk of overuse and environmental contamination. Secondly, the prolonged release of the active ingredient ensures that the pesticide remains effective for a longer period, reducing the need for frequent reapplication.

Figure 8:
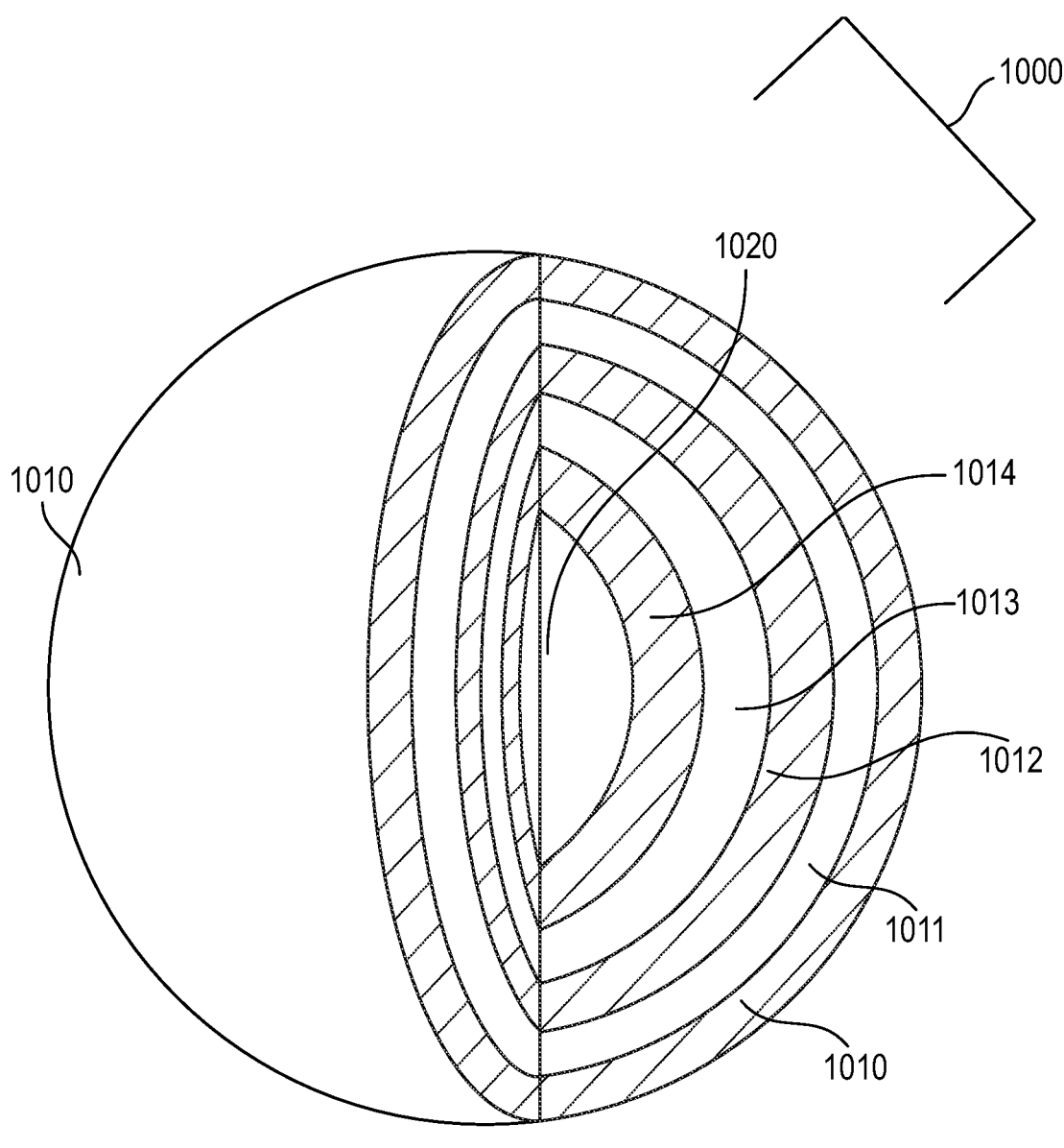
FIG. 8 is a sectional representative view of the cross-section of a 6-layer multi-layer chitosan encapsulated nanoparticle sphere.

FIG. 8 is a cross-sectional representative view of the cross-section of a 6-layer multi-layer chitosan encapsulated nanoparticle sphere. This representation of a 6-layer nanosphere 1000 shows a nanosphere core 1020, a chitosan outermost layer 1010, a second outermost layer 1011 right below the outermost layer 1010, a third outermost layer 1012 right below the second outermost layer 1011, a fourth outermost layer 1013 right below the third outermost layer 1012, and a fourth outermost layer 1014 right below the third outermost layer 1013. In this depiction, the fourth outermost layer is touching the nanoparticle core 1020.

The shaded layers are representative of the layers that contain chitosan (1010, 1012, 1014). The non-shaded layers represent layers that contain active ingredients or a mixture of active ingredients (1011, 1013). The nanosphere core 1020 is made of an active ingredient or mixture of active ingredients. Some embodiments include a nanosphere core that includes chitosan (this would cause an odd number of layers because the outermost layer must be chitosan). Some embodiments include a chitosan/crosslinking-agent shell in place of the chitosan shell. Some embodiments include the use of other substances combined with the active ingredients (fillers, extenders, wetting agents, disintegrants, and surfactants) in each layer and in the nanoparticle core 1020. Once chitosan containing layers degrade, they release the compounds (and the active ingredients) in the layer right below them.

FIG. 9 is a cross-sectional representative view of the cross-section of a 10-layer multi-layer chitosan encapsulated nanoparticle sphere. This representation of a 10-layer nanosphere 1100 shows a nanosphere core 1020, a chitosan outermost layer 1010, a second outermost layer 1011 right below the outermost layer 1010, a third outermost layer 1012 right below the second outermost layer 1011, a fourth outermost layer 1013 right below the third outermost layer 1012, a fourth outermost layer 1014 right below the third outermost layer 1013, a fifth outermost layer 1015 right below the fourth outermost layer 1014, a sixth outermost layer 1016 right below the fifth outermost layer 1015, a seventh outermost layer 1017 right below the sixth outermost layer 1016, an eighth outermost layer 1018 right below the seventh outermost layer 1017, and a ninth outermost layer 1019 right below the eighth outermost layer 1018. In this depiction, the ninth outermost layer is touching the nanoparticle core 1020.

The shaded layers are representative of the layers that contain chitosan (1010, 1012, 1014, 1016, 1018). The non-shaded layers represent layers that contain active ingredients or a mixture of active ingredients (1011, 1013, 1015, 1017). The nanosphere core 1020 is made of an active ingredient or mixture of active ingredients. Some embodiments include a nanosphere core that includes chitosan (this would cause an odd number of layers because the outermost layer must be chitosan). Some embodiments include a chitosan/crosslinking-agent shell in place of the chitosan shell. Some embodiments include the use of other substances combined with the active ingredients (fillers, extenders, wetting agents, disintegrants, and surfactants) in each layer and in the nanoparticle core 1020. Once chitosan containing layers degrade, they release the compounds (and the active ingredients) in the layer right below them.

In addition to the described embodiments in FIGS. 8 and 9, it should be noted that other variations of the chitosan encapsulated nanoparticle sphere can have a different number of layers. The exact number of layers may vary based on the specific requirements and use considerations.

FIGS. 8 and 9 are meant to provide a visual aid to showcase two examples of a multi-layer chitosan encapsulated nanoparticle. It should be noted that these are not provided as the only examples of the inventive nanoparticle spheres, and that more embodiments with a different number of layers exist. For example, a multi-layer chitosan encapsulated nanosphere has been created with 128 layers, and it would be possible to create one with more layers.

Some embodiments include multi-layer wrapping/encapsulation of essential oils or absolute botanicals (less volatile, more pure essential oils). The multi-layer encapsulation technique used in the development of the pesticide product provides numerous advantages over traditional formulations. The unique approach results in a more stable pesticide with a longer shelf life and active lifetime, making it an ideal solution for farmers and agricultural businesses.

The multi-layer encapsulation technology allows for the gradual release of the active ingredient over time, ensuring a more controlled and effective delivery of the pesticide. This controlled release mechanism not only increases the overall efficiency of the product but also reduces the amount of pesticide needed, making it a more sustainable and environmentally friendly solution.

Chitosan is not only effective for encapsulating active ingredients, but it also has unique properties that make it an ideal material for use in agriculture. One such property is its ability to be absorbed by plants, which allows for the direct delivery of pesticides and/or nutrients to the plant system. This is particularly beneficial for controlling weeds, as the chitosan can slice through the cell walls of weeds to deposit the encapsulated pesticides. Additionally, chitosan can be sprayed onto the leaves and stems of beneficial plants to deliver nutrients without the need for root uptake.

Chitosan wrap at 5 nm—the plant recognizes the chitosan and it penetrates deeper without being attacked by the plant's internal systems. This may allow formulations that stimulate the repairing of cell walls, help with certain biotic processes to be administered to the plant internally. Some embodiments may include a formulation being brought into the plant through the roots to be spread throughout the rest of the plant.

Some embodiments may use chitosan as a chelator to bind and allow for more stability of the pesticides and fertilizers. This may also allow the fertilizers/pesticides to enter through biological tissue without being targeted by a pest's biological responses.

Chelation is a type of bonding of ions and molecules to metal ions. It involves the formation or presence of two or more separate coordinate bonds between a polydentate ligand and a single central metal atom. These ligands are called chelates, chelators, chelating agents, or sequestering agents.

Chelating agents can also be used in fertilizers to improve their efficiency and effectiveness in delivering nutrients to plants. Fertilizers contain essential nutrients such as nitrogen, phosphorus, and potassium that plants require for growth and development. However, these nutrients can become bound to the soil particles or other compounds in the soil, making them unavailable for plants to absorb.

Chelating agents can help to overcome this problem by forming a complex with the nutrient ions, which makes them more available to plants. Chelating agents are commonly used in fertilizers to increase the solubility and availability of micronutrients such as iron, manganese, and zinc, which are often deficient in soils.

One common chelating agent used in fertilizers is ethylenediaminetetraacetic acid (EDTA). EDTA is a synthetic organic compound that has a strong affinity for metal ions and can form stable complexes with them. When added to fertilizers, EDTA can chelate micronutrient ions such as iron, making them more available for plant uptake.

Other chelating agents that are used in fertilizers include diethylenetriaminepentaacetic acid (DTPA), ethylenediaminedisuccinic acid (EDDS), and hydroxyethylenediaminetriacetic acid (HEDTA). These chelating agents have different properties and are used for different applications depending on the specific nutrient requirements of the plants and the soil conditions. Some embodiments include using Iron Chelate (IDHA), or Fulvic acid as a chelating agent. Some embodiments include using chitosan as the main chelating agent. This is especially effective in acidic solutions.

What is claimed is:

1. A method of encapsulating a pesticidal active ingredient selected from the group consisting of a plant essential oil, a plant extract, an organic absolute botanical, and an organic essential oil, the method comprising:
   adding a first active ingredient to a centrifuge;
   adding a solution containing chitosan into the centrifuge;
   centrifuging the chitosan-active ingredient mixture to create nanoparticle spheres of a first diameter;
   collecting the nanoparticle spheres of a first diameter;

adding the nanoparticle spheres, a second active ingredient, and a solution containing chitosan into a centrifuge;
   centrifuging the mixture to create nanoparticle spheres having a second diameter larger than the first diameter; and
   collecting the nanoparticle spheres of a second diameter, wherein
      the centrifuge comprises a nozzle having an internal portion with a diameter of 0.2-0.6 millimeters and an external portion with a diameter of 0.7-1.0 millimeters, the centrifuge operates at 4000-8000 rps, and the centrifuge operates at 4000-8000 rps, and
      the resulting nanoparticle spheres form a formulation effective for protecting plants from pests.

2. The method of claim 1, wherein the first active ingredient is an organic essential oil or an organic absolute botanical.

3. The method of claim 1, wherein the first active ingredient and the second active ingredient are the same active ingredient.

4. The method of claim 1, wherein the first active ingredient is a plant essential oil or plant extract.

5. The method of claim 4, wherein the plant essential oil or plant extract is selected from the group consisting of oxymatrine, geraniol, castor oil, castor extract, linseed, cedar, cinnamon, mint, peppermint, citronella, clove, corn, rosemary, cottonseed, sesame, garlic, soybean, thyme, geranium, lemongrass, tea tree, white mineral oil, citrus, spearmint, and a mixture thereof.

6. The method of claim 1, wherein the nanoparticle spheres are collected as a solid powder or in a solution.

7. The method of claim 1, wherein the nanoparticle spheres having the second diameter have a diameter of 20-200 nm.

8. The method of claim 1, wherein the chitosan and active ingredient combine to form a mixture that is centrifuged at 6000 rps to obtain substantially spherical nanoparticles comprising chitosan-encapsulated active ingredient.

9. The method of claim 1, further comprising adding a diluent to the nanoparticle spheres after the second centrifugation step, the diluent being selected from the group consisting of water, dextrin, calcium carbonate, lactose, propylene glycol, liquid paraffin, and normal saline.

10. The method of claim 1, wherein the nanoparticle spheres having the second diameter are used in one of perfumes, lotions, medical treatments, sunscreens, and insect repellants.

11. A method of encapsulating an active ingredient selected from the group consisting of a plant essential oil, a plant extract, an organic absolute botanical, and an organic essential oil, the method comprising:
   adding a first composition including at least a first active ingredient to a centrifuge;
   adding a solution containing chitosan into the centrifuge;
   centrifuging the chitosan-active ingredient mixture to create nanoparticle spheres of a first diameter;
   collecting the nanoparticle spheres of the first diameter;
   adding the nanoparticle spheres, a second composition including at least a second active ingredient, and a solution containing chitosan into a centrifuge;
   centrifuging the chitosan-active ingredient mixture to create nanoparticle spheres of a second diameter larger than the first diameter; and
   collecting the nanoparticle spheres of a second diameter, wherein the centrifuge comprises a nozzle having an internal portion with a diameter of 0.2-0.6 mm and an external portion with a diameter of 0.7-1.0 mm, the centrifuge operates at 4000-8000 rps, and the resulting nanoparticle spheres form a formulation effective for protecting plants from pests.

12. The method of claim 11, wherein the first composition and second composition are the same composition.

13. The method of claim 11, wherein the plant essential oil or plant extract is selected from the group consisting of oxymatrine, geraniol, castor oil, castor extract, linseed, cedar, cinnamon, mint, peppermint, citronella, clove, corn, rosemary, cottonseed, sesame, garlic, soybean, thyme, geranium, lemongrass, tea tree, white mineral oil, citrus, spearmint, and a mixture thereof.

14. A method of chitosan encapsulation a pesticide active ingredient selected from the group consisting of a plant essential oil, a plant extract, an organic absolute botanical, and an organic essential oil, the method comprising:

adding a first composition including at least a first active ingredient to a centrifuge;

adding a solution containing chitosan into the centrifuge;

centrifuging the chitosan and the first active ingredient mixture to create a first set of nanoparticle spheres comprising a core formed from the first composition and a first layer containing chitosan;

collecting the first set of nanoparticle spheres;

adding the collected first set of nanoparticle spheres, a second composition including at least a second active ingredient, and a solution containing chitosan into a centrifuge;

centrifuging the mixture to create a second set of nanoparticle spheres comprising the core formed from the first composition, the first layer containing chitosan, a second layer formed from the second composition, and a third layer containing chitosan;

wherein the centrifuge comprises a nozzle having an internal portion with a diameter of 0.2-0.6 mm and an external portion with a diameter of 0.7-1.0 mm, and collecting the second set of nanoparticle spheres, wherein the centrifuge operates at 4000-8000 rps, and the resulting nanoparticle spheres form a formulation effective for protecting plants from pests.

15. The method of claim 14, further comprising adding additional alternating layers of the compositions containing the active ingredients and layers containing chitosan to the second set of nanoparticle spheres.

16. The method of claim 15, wherein the number of additional layers creates a total number of layers between 10 and 128 layers.

* * * * *